United States Patent
Evans et al.

(10) Patent No.: US 7,189,728 B2
(45) Date of Patent: *Mar. 13, 2007

(54) INHIBITORS OF DIPEPTIDYL PEPTIDASE IV

(75) Inventors: David Michael Evans, Southampton (GB); Gary Robert William Pitt, Tidworth (GB)

(73) Assignee: Ferring, BV, Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/221,129

(22) PCT Filed: Apr. 26, 2001

(86) PCT No.: PCT/GB01/01888

§ 371 (c)(1),
(2), (4) Date: Jan. 9, 2003

(87) PCT Pub. No.: WO01/81304

PCT Pub. Date: Nov. 1, 2001

(65) Prior Publication Data

US 2003/0216450 A1 Nov. 20, 2003

(30) Foreign Application Priority Data

Apr. 26, 2000 (GB) .................. 0010183.2

(51) Int. Cl.
*A61K 31/4905* (2006.01)
*A61K 31/44* (2006.01)
*A61K 31/40* (2006.01)
*A01N 43/40* (2006.01)
*A01N 43/36* (2006.01)

(52) U.S. Cl. .................. 514/255.05; 514/343; 514/423

(58) Field of Classification Search ................ 544/406; 546/169, 279.1; 548/540; 514/255.05, 343, 514/423

See application file for complete search history.

(56) References Cited

U.S. PATENT DOCUMENTS

| | | | |
|---|---|---|---|
| 4,696,913 A * | 9/1987 | Geiger et al. ................. | 514/15 |
| 5,939,560 A | 8/1999 | Jenkins et al. | |
| 6,011,155 A * | 1/2000 | Villhauer .................... | 544/333 |
| 6,548,481 B1 * | 4/2003 | Demuth et al. ............... | 514/19 |
| 6,716,843 B2 * | 4/2004 | De Nanteuil et al. ..... | 514/237.2 |

FOREIGN PATENT DOCUMENTS

| | | | |
|---|---|---|---|
| DE | 198 26 972 A | | 12/1999 |
| DE | 199 40 130 A | | 3/2001 |
| EP | 0 490 379 A | | 6/1992 |
| WO | WO 88/19998 | * | 5/1998 |
| WO | WO 99 61431 A | | 12/1999 |

OTHER PUBLICATIONS

Translation of WO 99/61431, Schreiber Translations, Inc., PTO-05-3456, May 2005.*
Reinhold, D. et al., "Inhibitors of Dipeptidase IV (DP IV, CD26) Specifically Suppress Proliferation and Modulate Cytokine Production of Strongly CD26 Expressing U937 Cells", *Immunobiology*, Fischer, Stuttgart, DE, vol. 192, No. 1/02, 1994, pp. 121-136, XP000870158, ISSN: 0171-2985.
Augustyns, K. et al., "The Unique Properties of Dipeptidyl-Peptidase IV (DPP IV/CD26) and the Therapeutic Potential of DPP Inhibitors", *Current Medicinal Chemistry*, Be, Bentham Science Publishers BV, vol. 6, No. 4, 1999, pp. 311-327, XP000870290, ISSN: 09298673.
Ashworth, D.M. et al., "2-Cyanopyrrolidides as Potent, Stable Inhibitors of Dipeptidyl Peptidase IV", *Bioorganic & Medical Chemistry Letters*, Oxford, GB, vol. 6, No. 10, 1996, pp. 1163-1166, XP000953254, ISSN: 0960-894X.
Ashworth, D.M. et al., "4-Cyanothlazolidides As Very Potent, Stable Inhibitors of Dipeptidyl Peptidase IV", *Bioorganic & Medicinal Chemistry Letters*, Oxford, GB, vol. 6, No. 22, 1996, pp. 2745-2748,, XP000957892, ISSN:0960-894X.
Schoen, E. et al., "Dipeptidyl Peptidase IV in The Immune System. Effects of Specific Enzyme on Activity of Dipeptidyl Peptidase IV and Proliferation of Human Lymphocytes", *Biological Chemistry*, Hoppe-Seyler, De, Walter DE Gruyter, Berlin, vol. 372, No. 5, May 1991, pp. 305-311, XP000874047, ISSN: 0177-3593.
Demuth, H.-U. et al., Design of (Omega-N-(O-Acyl)Hydroxy Amid) Aminodicarboxylic Acid Pyrrolidides As Potent Inhibitors of Proline-Specific Peptidases:, *FEBS Letters*, Elsevier Science Publishers, Amsterdam, NL, vol. 320, No. 1, Mar. 1993, pp. 23-27, XP001007983, ISSN: 0014-5793.

* cited by examiner

Primary Examiner—Zachary C. Tucker
(74) Attorney, Agent, or Firm—Foley & Lardner LLP

(57) ABSTRACT

Compounds according to general formula (1), wherein $R^1$ is H or CN, $X^1$ is S, O, $SO_2$ or $CH_2$, $X^2$ is O, S or $CH_2$, $X^3$ is $NR^5$ or a carbonyl or thiocarbonyl group and $R^4$ is $R^6R^7N$, $R^8(CH_2)_qOC(=O)$, $R^8(CH_2)_qOC(=S)$, $R^6R^7NC(=O)$, $R^6R^7NC(=S)$; $R^8(CH_2)_qC(=O)$, $R^8(CH_2)_qC(=S)$ or $R^8(CH_2)_qSO_2$, m is 1–3 and n is 0–4 are new. The compounds of the invention are inhibitors of dipeptidyl peptidase IV. Pharmaceutical compositions of the compounds of the invention, or pharmaceutically acceptable salts thereof, are useful in the treatment of, inter alia, type 2 diabetes

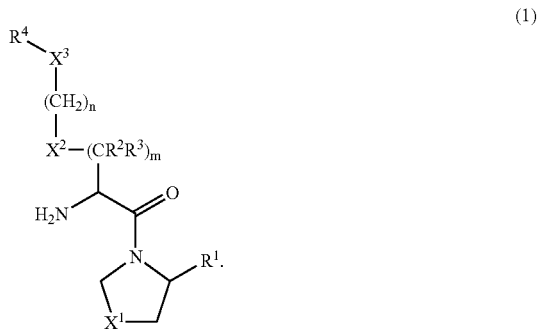

(1)

26 Claims, No Drawings

INHIBITORS OF DIPEPTIDYL PEPTIDASE IV

The present invention relates to a series of novel compounds that are inhibitors of the enzyme dipeptidyl peptidase IV, to pharmaceutical compositions comprising these inhibitors, and the use of such compositions in the treatment of human diseases.

BACKGROUND

The enzyme dipeptidyl peptidase IV, herein abbreviated DP-IV (and elsewhere as DAP-IV or DPP-IV) and also known by the classification EC.3.4.14.5, is a serine protease that cleaves the N-terminal dipeptide from peptides that begin with the sequence H-Xaa-Pro (where Xaa is any amino acid, although preferably a lipophilic one, and Pro is proline). It will also accept as substrates peptides that begin with the sequence H-Xaa-Ala (where Ala is alanine). DP-IV was first identified as a membrane-bound protein. More recently a soluble form has been identified.

Initial interest in DP-IV focussed on its role in the activation of T lymphocytes. DP-IV is identical to the T cell protein CD26. It was proposed that inhibitors of DP-IV would be capable of modulating T cell responsiveness, and so could be developed as novel immunomodulators. It was further suggested that CD26 was a necessary co-receptor for HIV, and thus that DP-IV inhibitors could be useful in the treatment of AIDS.

Attention was given to the role of DP-IV outside the immune system. It was recognised that DP-IV has a key role in the degradation of several peptide hormones, including growth hormone releasing hormone (GHRH) and glucagon-like peptide-1 and -2 (GLP-1 and GLP-2). Since GLP-1 is known to have a potentiating effect on the action of insulin in the control of post-prandial blood glucose levels it is clear that DP-IV inhibitors might also be usefully employed in the treatment of type II diabetes and impaired glucose tolerance. At least two DP-IV inhibitors are currently undergoing clinical trials to explore this possibility.

Several groups have disclosed inhibitors of DP-IV. While some leads have been found from random screening programs, the majority of the work in this field has been directed towards the investigation of substrate analogs. Inhibitors of DP-IV that are substrate analogs are disclosed in, for example, U.S. Pat. No. 5,462,928, U.S. Pat. No. 5,543,396, WO95/15309 (equivalent to U.S. Pat. No. 5,939,560 and EP 0731789), WO98/119998 (equivalent to U.S. Pat. No. 6,011,155), WO99/46272 and WO99/61431. The most potent inhibitors are aminoacyl pyrrolidine boronic acids, but these are unstable and tend to cydise, while the more stable pyrrolidine and thiazolidine derivatives have a lower affinity for the enzyme and so would require large doses in a clinical situation. Pyrrolidine nitrites appear to offer a good compromise since they have both a high affinity for the enzyme and a reasonably long half-life in solution as the free base. There remains, however, a need for inhibitors of DP-IV with improved properties.

BRIEF DESCRIPTION OF THE INVENTION

The present invention relates to a series of inhibitors of DP-IV with improved affinity for the enzyme. The compounds can be used for the treatment of a number of human diseases, including impaired glucose tolerance and type II diabetes. Accordingly, the invention further relates to the use of the compounds in the preparation of pharmaceutical compositions, to such compositions per se, and to the use of such compositions in human therapy. The compounds of the invention are described by general formula 1.

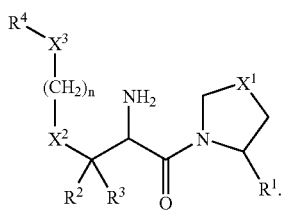

1

In general formula 1, $X^1$ is selected from —S—, —O—, —SO—, —SO$_2$— and —CH$_2$—; $X^2$ is selected from —O—, —S—, —NH— and —CH$_2$—; $X^3$ is either —NR$^5$— or a >C=O or >C=S group; $R^1$ is either H or —CN; $R^2$ and $R^3$ are independently selected from H and lower alkyl, or together may be —(CH$_2$)$_p$—; $R^4$ is $R^{4A}$ when $X^3$ is —NR$^5$— and $R^{4B}$ when $X^3$ is >C=O or >C=S; $R^{4A}$ is selected from $R^6R^7$NC(=O), $R^6R^7$NC(=S); $R^8$(CH$_2$)$_q$C(=O), $R^8$(CH$_2$)$_q$C(=S), $R^8$(CH$_2$)$_q$SO$_2$, $R^8$(CH$_2$)$_q$OC(=S) and $R^8$(CH$_2$)$_q$OC(=O); $R^{4B}$ is $R^6R^7$N; $R^5$ is H or lower alkyl; $R^6$ and $R^7$ are each independently $R^8$(CH$_2$)$_q$ or together they are —(CH$_2$)$_2$-Z-(CH$_2$)$_2$—; $R^8$ is selected from H, alkyl, optionally substituted aryl, optionally substituted aroyl, optionally substituted arylsulphonyl and optionally substituted heteroaryl; Z is selected from a covalent bond, —(CH$_2$)$_r$—, —O—, —SO$_t$— and —N((CH$_2$)$_q$R$^8$)—; n is 0–4; p is 2–5; q is 0–3; r is 1 or 2; and t is 0–2.

DETAILED DESCRIPTION OF THE INVENTION

In a first aspect, the present invention comprises a series of novel compounds that are inhibitors of the enzyme DP-IV and are useful for the treatment of certain human diseases. The compounds are described by general formula 1.

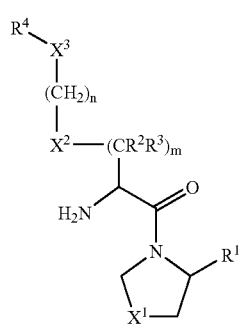

1

In general formula 1, $X^1$ is a divalent group selected from a sulphur atom (—S—), an oxygen atom (—O—), a sulphinyl group (—SO—), a sulphonyl group (—SO$_2$—) and a methylene group (—CH$_2$—). $X^2$ is a divalent group selected from an oxygen atom (—O—), a sulphur atom (—S—) and a methylene group (—CH$_2$—). $X^3$ is either a substituted imino group (—NR$^5$—) or a carbonyl (>C=O) or thiocarbonyl (>C=S) group.

$R^1$ is either a hydrogen atom (H) or a nitrile group (—CN).

$R^2$ and $R^3$ may each independently of the other be a hydrogen atom or a lower alkyl group, or together they may be a chain of between two and five methylene units ($—(CH_2)_p—$ where p is in the range 2–5) so as to form, with the carbon atom to which they are attached, a three, four, five or six-membered ring. The value of m may be 1, 2 or 3. When m is greater than 1 then each $CR^2R^3$ unit may be the same or different. For example, when m is 2 then $(CR^2R^3)_2$ may be $CH_2CH_2$, $CH_2C(Me)_2$, $C(Me)_2CH_2$ and the like.

The nature of $R^4$ depends on the identity of $X^3$, such that the two groups are linked by an amide (CO—N), thioamide (CS—N) or sulphonamide ($SO_2$—N) bond. So, when $X^3$ is a substituted imino group ($—NR^5—$) then $R^4$ is $R^{4A}$, where $R^{4A}$ is selected from carbamoyl groups ($R^6R^7NC(=O)$), thiocarbamoyl groups ($R^6R^7NC(=S)$); optionally modified acyl groups ($R^8(CH_2)_qC(=O)$), optionally modified thioacyl groups ($R^8(CH_2)_qC(=S)$), sulphonyl groups ($R^8(CH_2)_qSO_2$), optionally modified (alkyl or aryloxy)carbonyl groups ($R^8(CH_2)_qOC(=O)$) and optionally modified (alkyl or aryloxy)thiocarbonyl groups($R^8(CH_2)_qOC(=S)$). As used herein, the term "optionally modified" is taken to indicate that some embodiments of $R^8$ are beyond the scope of the terms "alkyl", "acyl" and "aryl". The scope of the definition of $R^{4A}$ is determined by the scope of the definition of $R^8$. Alternatively, when $X^3$ is a carbonyl (>C=O) or thiocarbonyl (>C=S) group then $R^4$ is $R^{4B}$, where $R^{4B}$ is a substituted amino group ($R^6R^7N$).

$R^5$ is a hydrogen atom (H) or a lower alkyl group. Preferably, $R^5$ is H.

$R^6$ and $R^7$ may each independently of the other be $R^8(CH_2)_q$. Alternatively, they may together be a group $—(CH_2)_2-Z^1-(CH_2)_2—$ or $—CHR^9-Z^2-CH_2—CR^{10}—$. Here $Z^1$ is a covalent bond, a methylene or ethylidene group ($—(CH_2)_r—$ where r is 1 or 2), an oxygen atom (—O—), a sulphur or oxidised sulphur atom ($—SO_t—$ where t is zero, 1 or 2) or a substituted imino group ($—N((CH_2)_qR^8)—$), such that the group $NR^6R^7$ is a pyrrolidine, piperidine, perhydroazepine, morpholine, optionally oxidised thiomorpholine or substituted piperazine ring. $Z^2$ is an ortho-phenylene moiety ($—C_6H_4—$), such that the group $NR^6R^7$ is a tetrahydroisoquinoline.

$R^8$ is selected from a hydrogen atom (H), a lower alkyl group, a benzo-fused lower cycloalkyl group (such as an indanyl group), an acyl (lower alkyl-CO) group, a di(lower alkyl)amino group, a di(lower alkyl)carbamoyl group, an N-(lower alkyl)piperidinyl group, an optionally substituted α-alkylbenzyl group, an optionally substituted phenyl, naphthyl or heteroaryl group, and an optionally substituted aroyl (aryl-CO) or arylsulphonyl (aryl-$SO_2$) group. In the foregoing, suitable optional substituents are lower alkyl, aryl which may be further substituted with one or more methyl or trifluoromethyl groups, hydroxy, lower alkyloxy, lower alkylsulphonyl, acyl, perfluoroacyl, amino, lower alkylamino, di(lower alkyl)amino, aminoalkylene, fluoro, chloro, bromo, trifluoromethyl, nitro, cyano, carbamoyl, carboxy and lower alkyloxycarbonyl groups. In addition, two adjacent substituents may be linked so as to form a ring fused to the parent aryl or heteroaryl ring.

$R^9$ and $R^{10}$ are independently selected from hydrogen, carbamoyl, hydroxymethyl and cyanomethyl groups.

The integer n is selected from the range zero to 4, and q is selected from the range zero to 3.

Certain compounds are specifically excluded from the scope of the present invention. When $X^2$ is methylene, $X^3$ is NH and $R^4$ is $R^8(CH_2)_qO(CO)$, with q=1, then $R^8$ may not be unsubstituted phenyl or phenyl substituted with a nitro group. It is generally preferred that when $X^2$ is methylene, $X^3$ is NH, $R^4$ is $R^8(CH_2)_qO(CO)$, q is 1 and $R^8$ is a substituted phenyl group then the substituent or substituents should be selected from chloro, methoxy and trifluoromethyl groups.

In the context of the present disclosure, the term lower alkyl, either by itself or in such combinations as lower alkyloxy, is intended to comprise linear, branched and cyclic saturated hydrocarbon groups of between one and six carbon atoms. Examples of lower alkyl groups include, but are not limited to, methyl, ethyl, isopropyl, tert-butyl, neopentyl, cyclohexyl, cyclopentylmethyl, 2-(cyclopropyl)ethyl, 3,3-dimethylcyclobutyl and bicyclo[3.1.0]hexyl.

The term heteroaryl includes monocyclic five- and six-membered ring aromatic groups with one or two heteroatoms, which are selected from nitrogen, oxygen and sulphur. Thus, heteroaryl groups include pyridyl, pyridazinyl, pyrimidinyl, pyrazinyl, pyrrolyl, thienyl, furyl, imidazolyl, pyrazolyl, thiazolyl, isothiazolyl, oxazolyl and isoxazolyl. Heteroaryl further includes the benzofused derivatives of these rings, such as quinolinyl, isoquinolinyl, quinoxalinyl, quinazolinyl, phthalazinyl, cinnolinyl, indolyl, isoindolyl, benzothiazolyl and the like, and bicyclic groups formed by the fusion of two such monocyclic heteroaromatic groups.

The term aryl includes phenyl, naphthyl and heteroaryl.

The compounds of general formula 1 have at least one stereogenic centre and so can exhibit optical isomerism. All such isomers, including enantiomers, diastereomers and epimers are included within the scope of the invention. Furthermore, the invention includes such compounds as single isomers and as mixtures, including racemates. Certain compounds according to general formula 1, including those with a heteroaryl group which carries a hydroxy or amino substituent, can exist as tautomers. These tautomers, either separately or as mixtures, are also considered to be within the scope of the invention.

The compounds according to general formula 1 have at least one basic functional group. They can therefore form addition salts with acids. Those addition salts that are formed with pharmaceutically acceptable acids are included within the scope of the invention. Examples of suitable acids include acetic acid, trifluoroacetic acid, citric acid, fumaric acid, benzoic acid, pamoic acid, methanesulphonic acid, hydrochloric acid, nitric acid, sulphuric acid, phosphoric acid and the like.

Certain compounds according to general formula 1 have an acidic group and so are able to form salts with bases. Examples of such salts include the sodium, potassium and calcium salts, which are formed by the reaction of the acid with the corresponding metal hydroxide, oxide, carbonate or bicarbonate. Similarly, tetra-alkyl ammonium salts may be formed by the reaction of the acid with a tetra-alkyl ammonium hydroxide. Primary, secondary and tertiary amines, such as triethylamine, can form addition salts with the acid. A particular case of this would be an internal addition salt formed between an acidic group and the primary amine group of the same molecule, which is also called a zwitterion. Insofar as they are pharmaceutically acceptable, all these salts are included within the scope of the invention.

In a preferred embodiment of the invention $R^1$ is a nitrile group. Within this embodiment, it is preferred that the stereochemistry of the nitrile group is as shown in general formula 2.

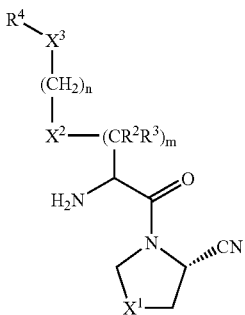

According to the standard terminology, this is the S configuration when $X^1$ is methylene but the R configuration when $X^1$ is sulphur, oxygen, sulphinyl or sulphonyl.

In another preferred embodiment, the stereochemistry at the centre adjacent to the primary amine is as shown in general formula 3. This is the S configuration when $X^2$ is an oxygen atom or a methylene or imino group, and the R configuration when $X^2$ is a sulphur atom.

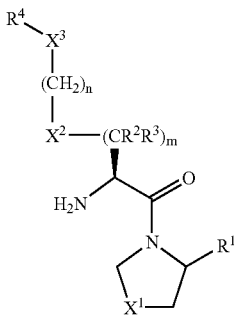

Within this embodiment, it is more preferred that $R^1$ should be a nitrile group, and more preferred still that it should have the absolute configuration depicted in general formula 4.

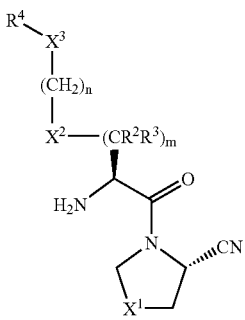

In another preferred embodiment of the invention, m is 1. More preferably m is 1 and $R^2$ and $R^3$ are independently hydrogen atoms or methyl groups. When $X^2$ is a methylene group, it is more preferred that $R^2$ and $R^3$ both be hydrogen. When $X^2$ is an oxygen atom, it is more preferred that one of $R^2$ and $R^3$ be hydrogen and the other a methyl group. When $X^2$ is a sulphur atom, it is more preferred that both $R^2$ and $R^3$ be methyl groups.

In another preferred embodiment, $X^1$ is either S or methylene. More preferably, $X^1$ is S and $R^1$ is H, or $X^1$ is methylene and $R^1$ is CN.

In another preferred embodiment, $X^3$ is NH. More preferably, $X^3$ is NH, m is 1, $R^2$ and $R^3$ are both H, $X^2$ is methylene and n is 1 or 2.

In another preferred embodiment, $R^4$ is $R^6$NHCO or $R^8$CO and $R^8$ is an optionally substituted heteroaryl group. More preferably, $R^8$ is an unsubstituted heteroaryl group, or a heteroaryl group substituted with one or two groups chosen from lower alkyl, lower alkyloxy, fluoro, chloro and trifluoromethyl groups.

In another preferred embodiment, $X^3$ is CO and $R^4$ is $R^8$NH. More preferably $R^8$ is an optionally substituted heteroaryl group. More preferably still, $R^8$ is an unsubstituted heteroaryl group, or a heteroaryl group substituted with one or two groups chosen from lower alkyl, lower alkyloxy, fluoro, chloro and trifluoromethyl groups.

In another preferred embodiment, $X^3$ is NH and $R^4$ is selected from $R^6R^7N(CO)$, $R^8(CH_2)_qCO$ and $R^8(CH_2)_qSO_2$.

Particularly preferred compounds within the invention include:

(2S)-1-[N$^\omega$-(Pyrazinyl-2-carbonyl)-L-ornithinyl]pyrrolidine-2-carbonitrile,
(2S)-1-[N$^\omega$-(Pyrazinyl-2-carbonyl)-L-lysinyl]pyrrolidine-2-carbonitrile,
(2S)-1-[(2'S)-2'-Amino-4'-(pyrazinyl-2''-carbonylamino)butanoyl]pyrrolidine-2-carbonitrile,
(4R)-3-[N$^\omega$-(Pyrazinyl-2-carbonyl)-L-lysinyl]thiazolidine-4-carbonitrile,
(2S)-1-[N$^\omega$-(Pyridyl-3-methyl)-L-glutaminyl]pyrrolidine-2-carbonitrile,
1-[N$^\omega$-(Pyrazinyl-2-carbonyl)-L-ornithinyl]pyrrolidine,
(2S)-1-[S-(Acetylaminomethyl)-L-cysteinyl]pyrrolidine-2-carbonitrile,
3-[N$^\omega$-(2-Chloropyridyl-3-carbonyl)-L-ornithinyl]thiazolidine,
1-[N$^\omega$-(2-Chloropyridyl-3-carbonyl)-L-ornithinyl]pyrrolidine, and
(2S)-1-[N$^\omega$-(2-Chloropyridyl-3-carbonyl)-L-ornithinyl]pyrrolidine-2-carbonitrile
3-[N$^\omega$-(Pyrazinyl-2-carbonyl)-L-ornithinyl]thiazolidine,
3-[N$^\omega$-(2-Quinoxaloyl)-L-lysinyl]thiazolidine,
3-[N$^\omega$-(2-Quinoxaloyl)-L-ornithinyl]thiazolidine,
(2S)-1-[N$^\omega$-(2-Quinoxaloyl)-L-ornithinyl]pyrrolidine-2-carbonitrile,
3-[N$^\omega$-(6-Methylpyrazinyl-2-carbonyl)-L-ornithinyl]thiazolidine,
3-[N$^\omega$-(Isoquinoline-3-carbonyl)-L-ornithinyl]thiazolidine,
3-[N$^\omega$-(6-Trifluoromethylnicotinoyl)-L-ornithinyl]thiazolidine,
(2S)-1-[(2'R)-3'-(Acetylaminomethylthio)-2'-amino-3'-methylbutanoyl]pyrrolidine-2-carbonitrile,
(2S)-1-[S-(3-Picolylcarbamoylmethyl)-L-cysteinyl]pyrrolidine-2-carbonitrile,
3-[N$^\omega$-(3-Pyridyloxycarbonyl)-L-ornithinyl]thiazolidine,
3-[O-(3-Chlorobenzylcarbamoyl)serinyl]thiazolidine, and
3-[(2'S)-2'-Amino-5'-oxo-5'-(1'',2'',3'',4''-tetrahydroisoquinolin-2''-yl)pentanoyl]thiazolidine.

In a second aspect, the present invention comprises a pharmaceutical composition for human therapeutic use. The composition is characterised in that it has, as an active agent, at least one of the compounds described above. Such a composition is useful in the treatment of human diseases.

The composition will generally include one or more additional components selected from pharmaceutically acceptable excipients and pharmaceutically active agents other than those of the present invention.

The composition may be presented as a solid or liquid formulation, depending on the intended route of administration. Examples of solid formulations include pills, tablets, capsules and powders for oral administration, suppositories for rectal or vaginal administration, powders for nasal or pulmonary administration, and patches for transdermal or transmucosal (such as buccal) administration. Examples of liquid formulations include solutions and suspensions for intravenous, subcutaneous or intramuscular injection and oral, nasal or pulmonary administration. A particularly preferred presentation is a tablet for oral administration. Another preferred presentation, particularly for emergency and critical care, is a sterile solution for intravenous injection.

The composition comprises at least one compound according to the preceding description. The composition may contain more than one such compound, but in general it is preferred that it should comprise only one. The amount of the compound used in the composition will be such that the total daily dose of the active agent can be administered in one to four convenient dose units. For example, the composition can be a tablet containing an amount of compound equal to the total daily dose necessary, said tablet to be taken once per day. Alternatively, the tablet can contain half (or one third, or one quarter) of the daily dose, to be taken twice (or three or four times) per day. Such a tablet can also be scored to facilitate divided dosing, so that, for example, a tablet comprising a full daily dose can be broken into half and administered in two portions. Preferably, a tablet or other unit dosage form will contain between 0.1 mg and 1 g of active compound. More preferably, it will contain between 1 mg and 250 mg.

The composition will generally include one or more excipients selected from those that are recognised as being pharmaceutically acceptable. Suitable excipients include, but are not limited to, bulking agents, binding agents, diluents, solvents, preservatives and flavouring agents. Agents that modify the release characteristics of the composition, such as polymers that selectively dissolve in the intestine ("enteric coatings") are also considered in the context of the present invention, to be suitable excipients.

The composition may comprise, in addition to the compound of the invention, a second pharmaceutically active agent. For example, the composition may include an antidiabetic agent, a growth-promoting agent, an anti-inflammatory agent or an antiviral agent. However, it is generally preferred that the composition comprise only one active agent.

In a third aspect, the invention comprises a use for the compounds and compositions described above for the treatment of human diseases. This aspect can equally be considered to comprise a method of treatment for such diseases. The diseases susceptible to treatment are those wherein an inhibition of DP-IV or CD26 results in a clinical benefit either directly or indirectly. Direct effects include the blockade of T lymphocyte activation. Indirect effects include the potentiation of peptide hormone activity by preventing the degradation of these hormones. Examples of diseases include, but are not limited to, auto-immune and inflammatory diseases such as inflammatory bowel disease and rheumatoid arthritis, growth hormone deficiency leading to short stature, polycystic ovary syndrome, impaired glucose tolerance and type 2 diabetes. Particularly preferred is the use of the compounds and compositions for the treatment of impaired glucose tolerance and type 2 diabetes, and equally a method of treatment of these diseases by the administration of an effective amount of a compound or composition as previously described.

The precise details of the treatment, including the dosing regimen, will be established by the attending physician taking into account the general profile of the patient and the severity of the disease. For diseases such as inflammatory bowel disease that have acute phases of active disease separated by quiescent periods, the physician may select a relatively high dose during the acute phase and a lower maintenance dose for the quiescent period. For chronic diseases such as type 2 diabetes and impaired glucose tolerance, the dosing may need to be maintained at the same level for an extended period. A dosing schedule of one to four tablets per day, each comprising between 0.1 mg and 1 g (and preferably between 1 mg and 250 mg) of active compound might be typical in such a case.

The compounds according to the invention can be prepared by methods known in the art. The route chosen will depend on the particular nature of the substituents present in the target molecule. In the following general description the synthetic route is outlined for compounds wherein m is 1. Compounds with m=2 or 3 can generally be prepared by analogous routes.

The starting material will usually be an α,ω-diamino acid derivative 5 or an amino dicarboxylic acid derivative 6.

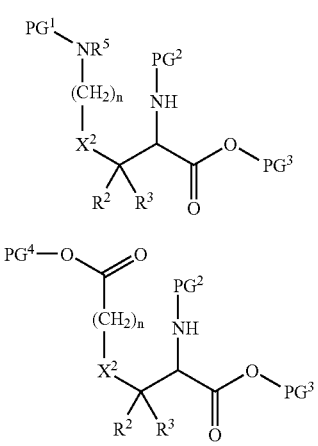

$PG^1$ and $PG^2$ are "orthogonal" protecting groups—groups that mask the reactivity of the amine groups and that can each be selectively removed in the presence of the other. Suitable groups are well known in the literature. $PG^3$ and $PG^4$ are protecting groups for carboxylic acids. They are chosen such that they are orthogonal to each other and to the amino protecting groups. Suitable possibilities for $PG^3$ and $PG^4$ are also well known in the literature. Derivatives of diamino acids according to general formula 5 and derivatives of amino dicarboxylic acids according to general formula 6 are either items of commerce, or can be prepared following methods described in the literature. In practice, and depending on the strategy chosen, the starting material will have only two of the three protecting groups present. Either $PG^3$ will be absent to allow the pyrrolidine (or thiazolidine or oxazolidine) residue to be introduced, or $PG^1$ or $PG^4$ will be absent to allow the side chain to be elaborated.

Scheme A illustrates the introduction of the pyrrolidine (or thiazolidine or oxazolidine) group as the first step in the preparation of the compounds of the invention.

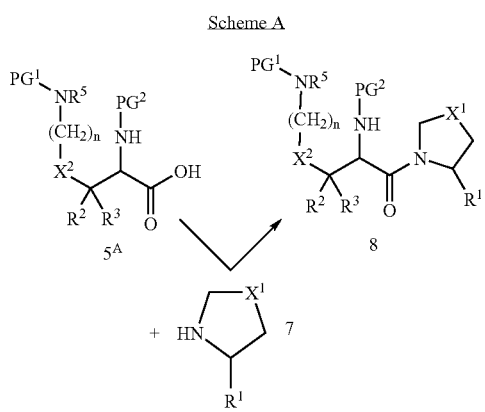

Scheme A

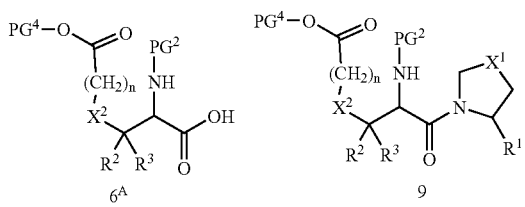

Compounds $5^A$ and $6^A$ correspond to 5 and 6 with $PG^3$ as a hydrogen atom (i.e. without the protecting group). The free carboxylic acid can be reacted with a pyrrolidine derivative 7 to give the amide 8 or 9. Reaction conditions for achieving this transformation are well known in the literature. Suitable reagents include carbodiimides, phosphorus reagents and alkyl chloroformates, and the reaction is usually catalysed by a tertiary amine such as triethylamine or dimethylaminopyridine.

The reaction depicted in Scheme A is available for all combinations of $R^1$ and $X^1$. However, for the case where $R^1$ is a nitrile group, or where $X^1$ is a sulphinyl or sulphonyl group, it may be advantageous to modify the strategy as depicted in Schemes B and C.

Scheme B

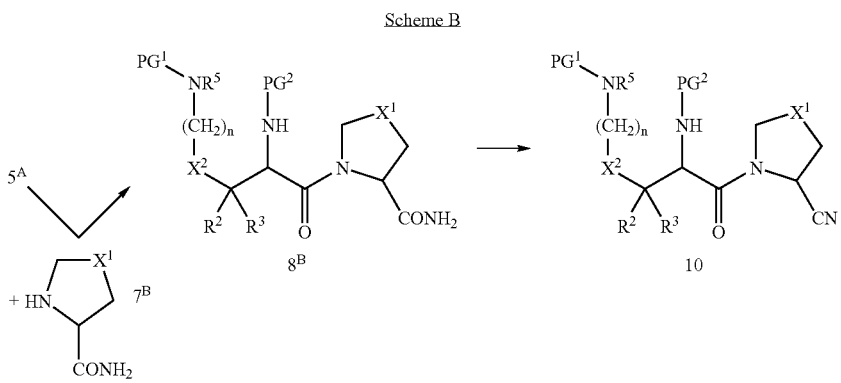

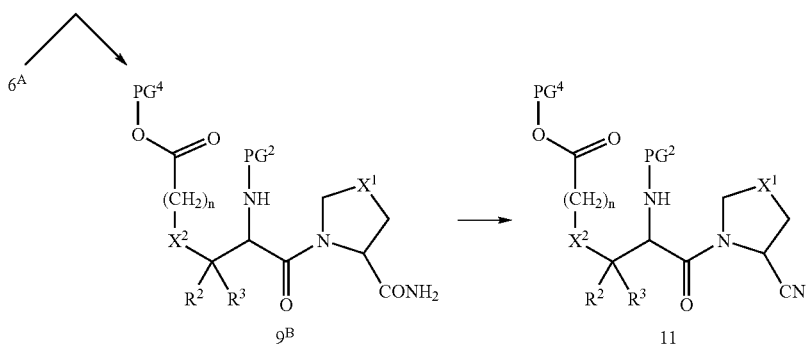

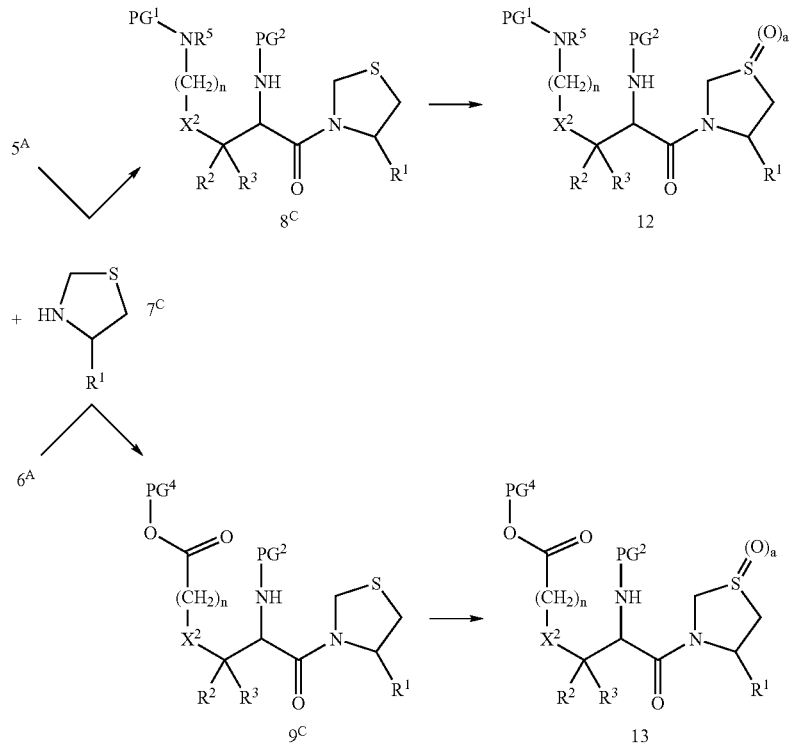

In Scheme B, the R¹ group is introduced as a primary amide and subsequently transformed into a nitrile by the action of a dehydrating agent such as trifluoroacetic anhydride. In Scheme C, the X¹ group is introduced as a thioether and subsequently transformed into a sulphoxide (a=1) or sulphone (a=2) by the action of an oxidant such as sodium periodate. The modification to the strategy afforded by Scheme C is not possible if X² is a sulphur atom.

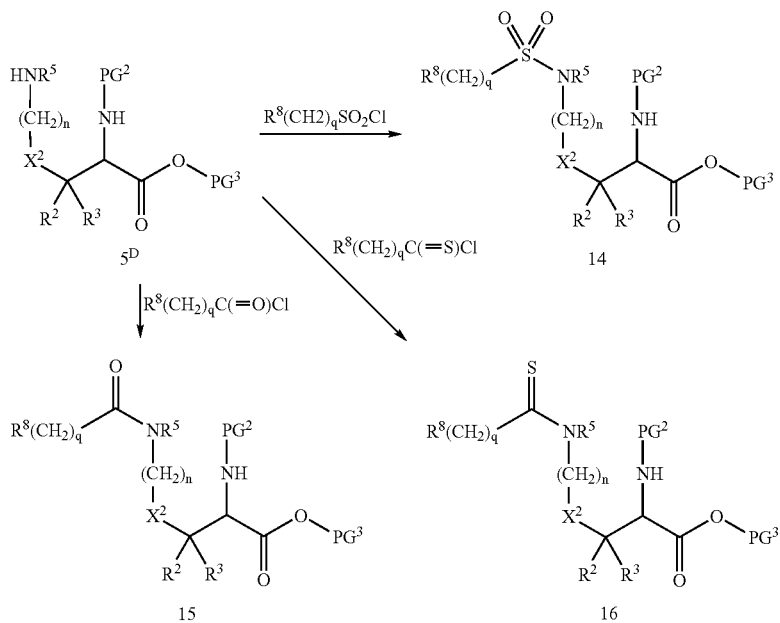

In Scheme D, compound $5^D$ is the diamino acid derivative 5 where the ω-protecting group is a hydrogen atom. The free amine group reacts readily with sulphonyl chlorides, acyl chlorides and thioacyl chlorides, usually in the presence of a tertiary amine, to produce sulphonamides 14, amides 15 and thioamides 16 respectively. The reagents are generally either available per se, or can be prepared from the corresponding acids. The reaction of scheme D is generally applicable to all the variations of the group $R^8(CH_2)_q$, with the proviso that certain of the substituents contemplated for the phenyl and heteroaryl rings which are options for $R^8$ may require protection. Such substituents and the appropriate protection will generally be obvious to those familiar with the art.

to the corresponding carbamoyl chloride 17 or thiocarbamoyl chloride 18 by reaction with phosgene or thiophosgene. Other reagents are known in the art to be functionally equivalent to these toxic reagents and they may also be used. When $R^5$ is hydrogen, the intermediate formed is an isocyanate or isothiocyanate, but this behaves functionally as an equivalent of the corresponding chloride. Intermediates 17 and 18 are not normally isolated, but are treated directly with alcohols to give carbamates 19 and thiocarbamates 20. Treatment of these same intermediates with amines leads to the formation of ureas 21 and thioureas 22. Alternatively, $5^D$ may be reacted directly with a chloroformate or chlorothioformate to give the carbamate or thiocarbamate, or, when neither $R^6$ nor $R^7$ is hydrogen, with a chloroformamide or chlorothioformamide to give the urea or thiourea. When $R^6$

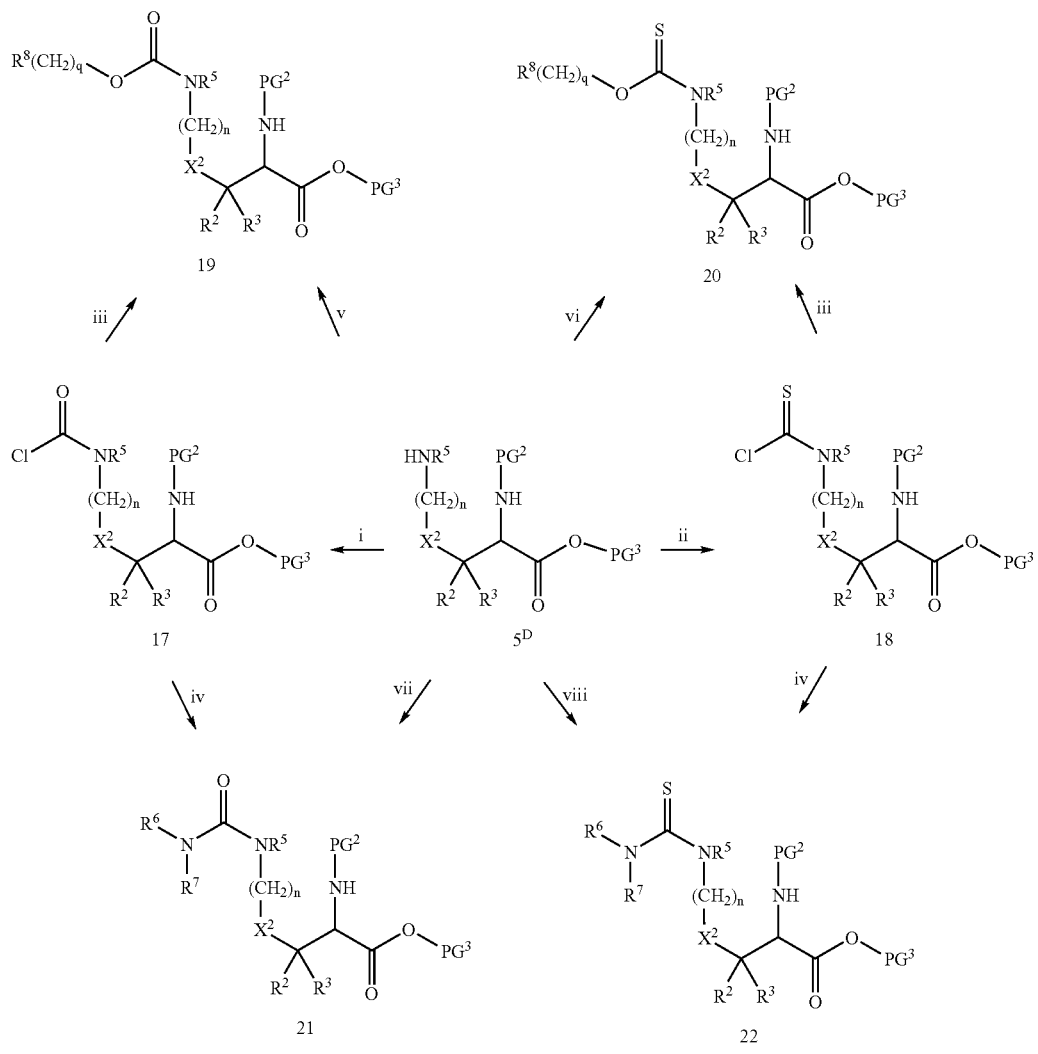

Scheme E

Reagents: i) $COCl_2$; ii) $CSCl_2$; iii) $R^8(CH_2)_qOH$; iv) $R^6R^7NH$; v) $R^8(CH_2)_qOCOCl$; vi) $R^8(CH_2)_qOCSCl$; vii) $R^6R^7NCOCl$; viii) $R^6R^7NCSCl$.

Scheme E illustrates the elaboration of $5^D$ to give carbamates and ureas, and their thio analogues. When $R^5$ is other than a hydrogen atom, compound $5^D$ can be converted or $R^7$ is a hydrogen atom the chloroformamide or chlorothioformamide will tend to be unstable, in which case the isocyanate (eg. $R^6$—NCO) or isothiocyanate (e.g. $R^6$—NCS) is used. As discussed previously for Scheme D, certain substituents within the embodiments of $R^8$ may require appropriate protection.

Scheme F

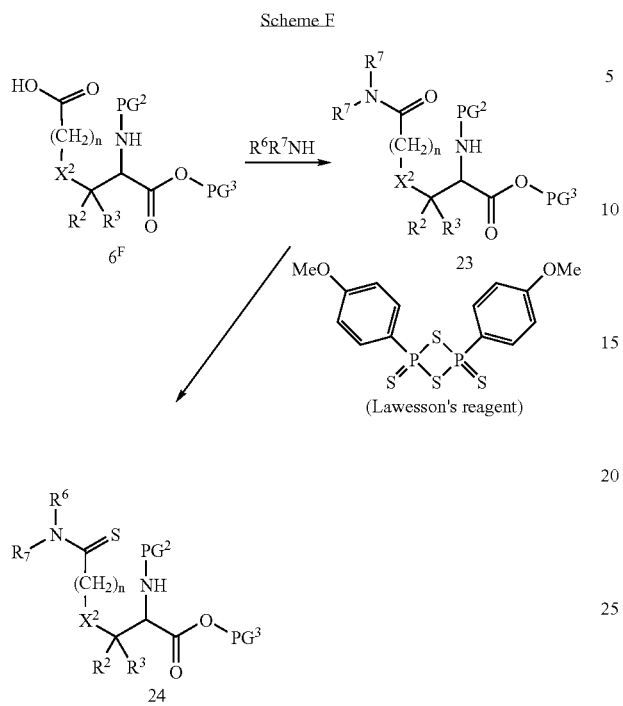

Scheme F illustrates the elaboration of the side chain of the amino dicarboxylic acid series. The ω-deprotected acid $6^F$ can be reacted under a variety of conditions with an amine to give amide 23. The condensation may be promoted by a dehydrating reagent such as a carbodiimide or a phosphorus reagent. Alternatively the acid may be converted into a more reactive derivative, such as by treatment with oxalyl chloride or thionyl chloride to give the corresponding acid chloride, which will react directly with an amine. The thioamide 24 may be obtained by treating the amide 23 with Lawesson's reagent.

When all the groups have been elaborated the final protecting group is removed and the product is isolated and purified using standard techniques.

These general methods are further illustrated in the following, non limiting examples.

EXAMPLES

Abbreviations

The following abbreviations have been used.

| | |
|---|---|
| DMF | N,N-Dimethyformamide |
| h | Hour(s) |
| hplc | High pressure liquid chromatography |
| min | Minute(s) |
| pet. ether | Petroleum ether fraction boiling at 60–80° C. |
| PyBOP ® | (Benzotriazol-1-yloxy)tripyrrolidinophosphonium hexafluorophosphate |
| PyBroP ® | Bromotripyrrolidinophosphonium hexafluorophosphate |
| TFA | Trifluoroacetic acid |

Example 1

(2S)-1-[N$^\omega$-(Pyrazinyl-2-carbonyl)-L-ornithinyl] pyrrolidine-2-carbonitrile trifluoroacetate

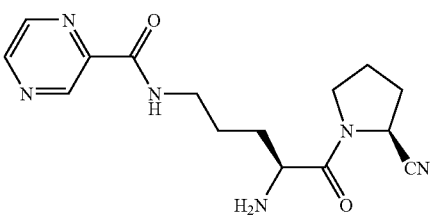

A. N-(2-Nitrobenzenesulphenyl)-L-proline

L-Proline (25 g, 217 mmol) was dissolved in 2M NaOH (110 mL, 220 mmol) and dioxan (120 mL). A solution of 2-nitrobenzenesulphenyl chloride (42 g, 222 mmol) in dioxan (60 mL) was slowly added at the same time as 2M NaOH (110 mL, 220 mmol). After 2 h at room temperature the reaction mixture was poured into water (500 mL) and the solid filtered off. The pH of the filtrate was adjusted to pH3 with 2M HCl and the solution was extracted with ethyl acetate (3×500 mL). The combined organic extracts were washed with water (4×200 mL) and brine (1×200 mL), dried (Na$_2$SO$_4$) and evaporated in vacuo to give an orange solid identified as N-(2-nitrobenzenesulphenyl)-L-proline (58.1 g, 217 mmol, 100%).

B. N-(2-Nitrobenzenesulphenyl)-L-proline succinimidyl ester

N-(2-Nitrobenzenesulphenyl)-L-proline (57.9 g, 216 mmol) was dissolved in CH$_2$Cl$_2$/DMF (9:1, 500 mL). N-Hydroxysuccinimide (37.3 g, 324 mmol) and water-soluble carbodiimide (51.8 g, 260 mmol) were added. After 18 h at room temperature the solvent was removed in vacuo and the residue was taken up in ethyl acetate (1000 mL). The solution was washed with water (4×200 mL) and brine (1×200 mL), dried (Na$_2$SO$_4$) and evaporated in vacuo to give a yellow solid identified as N-(2-nitrobenzenesulphenyl)-L-proline succinimidyl ester (78.9 g, 216 mmol, 100%).

C. N-(2-Nitrobenzenesulphenyl)-L-prolinamide

N-(2-Nitrobenzenesulphenyl)-L-proline succinimidyl ester (78.5 g, 215 mmol) was dissolved in dioxan (500 mL). Ammonia (35%, 100 mL) was added, After stirring at room temperature for 2 h the reaction mixture was poured into water (700 mL). The precipitate was filtered off, washed with water (200 mL), dried over P$_2$O$_5$ and recrystallised from ethyl acetate/pet ether to give a yellow solid identified as N-(2-nitrobenzenesulphenyl)-L-prolinamide (49.6 g, 185 mmol, 86%).

D. (2S)-N-(2-Nitrobenzenesulphenyl)pyrrolidine-2-carbonitrile

N-(2-Nitrobenzenesulphenyl)-L-prolinamide (49 g, 183 mmol) was dissolved in dry THF(300 mL). The solution was cooled to 0° C., triethylamine (36.7 g, 367 mmol) was added followed by the slow addition of trifluoroacetic anhydride (77 g, 367 mmol). The pH was adjusted to pH9 with triethylamine. After 30 min the reaction mixture was diluted with ethyl acetate (500 mL), washed with water (1×200 mL) and brine (1×200 mL), dried ($Na_2SO_4$) and evaporated in vacuo to give an orange oil which was purified by flash chromatography (eluant: 80% pet ether, 20% ethyl acetate) to give a yellow solid identified as (2S)-N-(2-nitrobenzenesulphenyl)pyrrolidine-2-carbonitrile (38.9 g, 150 mmol, 82%).

E. (2S)-Pyrrolidine-2-carbonitrile hydrochloride (2S)-N-(2-Nitrobenzenesulphenyl)pyrrolidine-2-carbonitrile (38.5 g, 149 mmol) was dissolved in diethyl ether (200 mL). 4M HCl/Dioxan (150 mL, 600 mmol) was slowly added. After 2 h at room temperature the reaction mixture was poured into diethyl ether (1000 mL). The solid was filtered off, washed with diethyl ether (500 mL) and recrystallised from methanol/diethyl ether to give a white solid identified as (2S)-pyrrolidine-2-carbonitrile hydrochloride (18.9 g, 142.5 mmol, 96%).

F. (2S)-1-[$N^\alpha$-(tert-Butyloxycarbonyl)-$N^\omega$-(pyrazinyl-2-carbonyl)-L-ornithinyl]-pyrrolidine-2-carbonitrile $N^\alpha$-(tert-Butyloxycarbonyl)-$N^\omega$-(pyrazinyl-2-carbonyl)-L-ornithine (2.5 g, 7.4 mmol) was dissolved in $CH_2Cl_2$ (50 mL). This solution was cooled to 0° C., (2S)-pyrrolidine-2-carbonitrile hydrochloride (1.2 g, 9.1 mmol) and PyBOP® (4.3 g, 8.23 mmol) were added, and the pH adjusted to pH9 with triethylamine. After 18 h at 0° C. to room temperature the solvent was removed in vacuo and the residue was taken up in ethyl acetate (200 mL). This solution was washed with 0.3M $KHSO_4$ (2×50 mL), sat. $NaHCO_3$ (2×50 mL), water (2×50 mL) and brine (1×50 mL), dried ($Na_2SO_4$) and evaporated in vacuo to give a yellow oil. This was purified by flash chromatography (eluant: 80% ethyl acetate, 20% pet. ether) to give a colourless oil identified as (2S)-1-[$N^\alpha$-(tert-butyloxycarbonyl)-$N^\omega$-(pyrazinyl-2-carbonyl)-L-ornithinyl]pyrrolidine-2-carbonitrile (2.98 g, 7.16 mmol, 97%).

G. (2S)-1-[$N^\omega$-(pyrazinyl-2-carbonyl)-L-ornithinyl]pyrrolidine-2-carbonitrile trifluoroacetate (2S)-1-[$N^\alpha$-tert-Butyloxycarbonyl-$N^\omega$-(pyrazinyl-2-carbonyl)-L-ornithinyl]pyrrolidine-2-carbonitrile (2.8 g, 6.7 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as (2S)-1-[$N^\omega$-(pyrazinyl-2-carbonyl)-L-ornithinyl]pyrrolidine-2-carbonitrile trifluoroacetate (1.5 g, 3.48 mmol, 52%).

[M+H]$^+$=317.3

Example 2

(2S)-1-[$N^\omega$-(Pyrazinyl-2-carbonyl)-L-lysinyl]pyrrolidine-2-carbonitrile trifluoroacetate

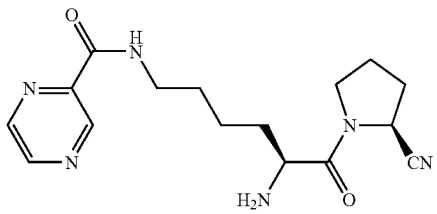

A. ($N^\alpha$-(tert-Butyloxycarbonyl)-$N^\omega$-(9-fluorenylmethyloxycarbonyl)-L-lysinyl)-L-prolinamide $N^\alpha$-(tert-Butyloxycarbonyl)-$N^\omega$-(9-fluorenylmethyloxycarbonyl)-L-lysine (5 g, 10.7 mmol) was dissolved in $CH_2Cl_2$ (100 mL). The solution was cooled to 0° C., L-prolinamide (1.78 g, 11.7 mmol) and PyBOP® (6.7 g, 12.8 mmol) were added, and the pH adjusted to pH9 with triethylamine. After 18 h at 0° C. to room temperature the solvent was removed in vacuo and the residue was taken up in ethyl acetate (200 mL). The solution was washed with 0.3M $KHSO_4$ (2×50 mL), sat. $NaHCO_3$ (2×50 mL), water (2×50 mL) and brine (1×50 mL), dried ($Na_2SO_4$) and evaporated in vacuo. The residue was purified by flash chromatography (eluant: 2% methanol, 98% chloroform) to give a colourless oil identified as ($N^\alpha$-(tert-butyloxycarbonyl)-$N^\omega$-(9-fluorenylmethyloxycarbonyl)-L-lysinyl)-L-prolinamide (4.05 g, 7.2 mmol, 67%).

B. (2S)-1-($N^\alpha$-(tert-Butyloxycarbonyl)-$N^\omega$-(9-fluorenylmethyloxycarbonyl)-L-lysinyl)-pyrrolidine-2-carbonitrile ($N^\alpha$-(tert-Butyloxycarbonyl)-$N^\omega$-(9-fluorenylmethyloxycarbonyl)-L-lysinyl)-L-prolinamide (3.95 g, 7.02 mmol) was dissolved in dry THF (100 mL). The solution was cooled to 0° C., triethylamine (1.4 g, 14 mmol) was added followed by the slow addition of trifluoroacetic anhydride (2.97 g, 14.1 mmol). The pH was adjusted to pH9 with triethylamine. After 30 min the reaction mixture was diluted with ethyl acetate (100 mL), washed with water (1×50 mL) and brine (1×50 mL), dried ($Na_2SO_4$) and evaporated in vacuo to give an orange oil. The residue was purified by flash chromatography (eluant: 60% pet ether, 40% ethyl acetate) to give a colourless oil identified as (2S)-1-($N^\alpha$-(tert-butyloxycarbonyl)-$N^\omega$-(9-fluorenylmethyloxycarbonyl)-L-lysinyl)pyrrolidine-2-carbonitrile (3.3 g, 6.11 mmol, 87%).

C. (2S)-1-($N^\alpha$(-tert-Butyloxycarbonyl)-L-lysinyl)pyrrolidine-2-carbonitrile (2S)-1-($N^\alpha$-(tert-Butyloxycarbonyl)-$N^\omega$-(9-fluorenylmethyloxycarbonyl)-L-lysinyl)pyrrolidine-2-carbonitrile (3.1 g, 5.7 mmol) was dissolved in THF (80 mL). Diethylamine (20 mL) was added. After 2 h at room temperature the solvent was removed in vacuo. The residue was purified by flash chromatography (eluant: 90% chloroform, 7% methanol, 3% triethylamine) to give a colourless oil identified as (2S)-1-(N$^\alpha$-(tert-butyloxycarbonyl)-L-lysinyl)pyrrolidine-2-carbonitrile (1.63 g, 5.03 mmol, 89%).

D. (2S)-1-(N$^\alpha$-(tert-Butyloxycarbonyl)-N$^\omega$-(pyrazinyl-2-carbonyl)-L-lysinyl)pyrrolidine-2-carbonitrile (2S)-1-(N$^\alpha$-(tert-Butyloxycarbonyl)-L-lysinyl)pyrrolidine-2-carbonitrile (100 mg, 0.31 mmol) was dissolved in CH$_2$Cl$_2$/DMF (9:1, 20 mL). To this solution at 0° C. was added 1-hydroxybenzotriazole hydrate (84 mg, 0.62 mmol), water-soluble carbodiimide (76 mg, 0.38 mmol), 2-pyrazinecarboxylic acid (43 mg, 0.35 mmol) and triethylamine (65 mg, 0.65 mmol). After 18 h at 0° C. to room temperature the solvent was removed in vacuo and the residue was taken up in ethyl acetate (70 mL). This solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo to give a yellow oil. The residue was purified by flash chromatography (eluant: 2% methanol, 98% chloroform) to give a colourless oil identified as (2S)-1-(N$^\alpha$-(tert-butyloxycarbonyl)-N$^\omega$-(pyrazinyl-2-carbonyl)-L-lysinyl)pyrrolidine-2-carbonitrile (124 mg, 0.29 mmol, 93%).

E. (2S)-1-[N$^\omega$-(Pyrazinyl-2-carbonyl)-L-lysinyl]pyrrolidine-2-carbonitrile trifluoroacetate (2S)-1-(N$^\alpha$-(tert-Butyloxycarbonyl)-N$^\omega$-(pyrazinyl-2-carbonyl)-L-lysinyl)pyrrolidine-2-carbonitrile (110 mg, 0.26 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as (2S)-1-[N$^\omega$-(pyrazinyl-2-carbonyl)-L-lysinyl]pyrrolidine-2-carbonitrile trifluoroacetate (66 mg).
[M+H]$^+$=331.1

Example 3

(4R)-3-[N$^\omega$-(Pyrazinyl-2-carbonyl)-L-lysinyl]thiazolidine-4-carbonitrile trifluoroacetate

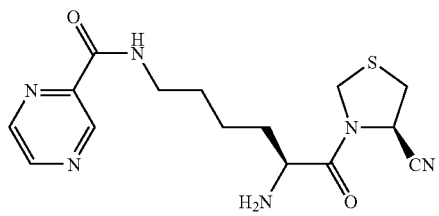

A. (4R)-3-(tert-Butyloxycarbonyl)thiazolidine-4-carboxamide (4R)-3-(tert-Butyloxycarbonyl)thiazolidine-4-carboxylic acid (12.5 g, 54.1 mmol) was dissolved in CH$_2$Cl$_2$/DMF (9:1, 150 mL). To this solution at 0° C. was added 1-hydroxybenzotriazole hydrate (14.6 g, 108 mmol) and water-soluble carbodiimide (13.0 g, 65 mmol). After 1 h at 0° C. ammonia (35%, 50 mL) was added. After 18 h at 0° C. to room temperature the solvent was removed in vacuo and the residue was taken up in ethyl acetate (500 mL). The solution was washed with 0.3M KHSO$_4$ (2×100 mL), sat. NaHCO$_3$ (2×100 mL), water (2×100 mL) and brine (1×100 mL), dried (Na$_2$SO$_4$) and evaporated in vacuo to give a yellow oil. The residue was purified by flash chromatography (eluant: 2% methanol, 98% chloroform) to give a colourless oil identified as (4R)-3-(tert-butyloxycarbonyl)thiazolidine-4-carboxamide (8.9 g, 38.4 mmol, 71%).

B. (4R)-Thiazolidine-4-carboxamide hydrochloride (4S)-3-(tert-Butyloxycarbonyl)thiazolidine-4-carboxamide (8.6 g, 37.1 mmol) was dissolved in 4M HCl/dioxan (50 mL). After 1 h at room temperature the solvent was evaporated in vacuo to give a white solid identified as (4R)-thiazolidine-4-carboxamide hydrochloride (6.2 g, 36.8 mmol, 99%).

C. (4R)-3-[N$^\alpha$-(tert-Butyloxycarbonyl)-N$^\omega$-(9-fluorenylmethyloxycarbonyl)-L-lysinyl]-thiazolidine-4-carboxamide N$^\alpha$-(tert-Butyloxycarbonyl)-N$^\omega$-(9-fluorenylmethyloxycarbonyl)-L-lysine (5 g, 10.7 mmol) was dissolved in CH$_2$Cl$_2$ (100 mL). This solution was cooled to 0° C., (4R)-thiazolidine-4-carboxamide hydrochloride (1.78 g, 11.7 mmol) and PyBOP® (6.7 g, 12.8 mmol) were added, and the pH was adjusted to pH9 with triethylamine. After 18 h at 0° C. to room temperature the solvent was removed in vacuo and the residue was taken up in ethyl acetate (200 mL). The solution was washed with 0.3M KHSO$_4$ (2×50 mL), sat. NaHCO$_3$ (2×50 mL), water (2×50 mL) and brine (1×50 mL), dried (Na$_2$SO$_4$) and evaporated in vacuo to give a yellow oil. The residue was purified by flash chromatography (eluant: 2% methanol, 98% chloroform) to give a colourless oil identified as (4R)-3-[N$^\alpha$-(tert-butyloxycarbonyl)-N$^\omega$-(9-fluorenylmethyloxycarbonyl)-L-lysinyl]thiazolidine-4-carboxamide (2.81 g, 4.8 mmol, 44%).

D. (4R)-3-[N$^\alpha$-(tert-Butyloxycarbonyl)-N$^\omega$-(9-fluorenylmethyloxycarbonyl)-L-lysinyl]-thiazolidine-4-carbonitrile (4R)-3-[N$^\alpha$-(tert-Butyloxycarbonyl)-N$^\omega$-(9-fluorenylmethyloxycarbonyl)-L-lysinyl]thiazolidine-4-carboxamide (2.7 g, 4.7 mmol) was dissolved in dry THF (100 mL). The solution was cooled to 0° C., triethylamine (1.0 g, 10 mmol) was added followed by the slow addition of trifluoroacetic anhydride (2.0 g, 9.5 mmol). The pH was adjusted to pH9 with triethylamine. After 30 min the reaction mixture was diluted with ethyl acetate (100 mL), washed with water (1×50 mL) and brine (1×50 mL), dried (Na$_2$SO$_4$) and evaporated in vacuo. The residue was purified by flash chromatography (eluant: 60% pet ether, 40% ethyl acetate) to give a colourless oil identified as (4R)-3-[N$^\alpha$-(tert-butyloxycarbonyl)-N$^\omega$-(9-fluorenylmethyloxycarbonyl)-L-lysinyl]thiazolidine-4-carbonitrile (2.14 g, 3.81 mmol, 82%).

E. (4R)-3-[N$^\alpha$-(tert-Butyloxycarbonyl)-L-lysinyl]thiazolidine-4-carbonitrile (4R)-3-[N$^\alpha$-(tert-Butyloxycarbonyl)-N$^\omega$-(9-fluorenylmethyloxycarbonyl)-L-lysinyl]thiazolidine-4-carbonitrile (1.9 g, 3.4 mmol) was dissolved in THF (40 mL). Diethylamine (10 mL) was added. After 2 h at room temperature the solvent was removed in vacuo. The residue was purified by flash chromatography (eluant: 90% chloroform, 7% methanol, 3% triethylamine) to give a colourless oil identified as (4R)-3-[N$^\alpha$-(tert-butyloxycarbonyl)-L-lysinyl]thiazolidine-4-carbonitrile (863 mg, 2.5 mmol, 75%).

F. (4R)-3-[N$^\alpha$-(tert-Butyloxycarbonyl)-N$^\omega$-(pyrazinyl-2-carbonyl)-L-lysinyl]thiazolidine-4-carbonitrile (4R)-3-[N$^\alpha$-(tert-Butyloxycarbonyl)-L-lysinyl]thiazolidine-4-carbonitrile (100 mg, 0.29 mmol) was dissolved in CH$_2$Cl$_2$ (20 mL). To this solution at 0° C. 2-pyrazinecarboxylic acid (43 mg, 0.35 mmol) and PyBOP® (170 mg, 0.33 mmol) were added and the pH was adjusted to pH9 with triethylamine. After 18 h at 0° C. to room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 2% methanol, 98% chloroform) to give a colourless oil identified as (4R)-3-[N$^\alpha$-(tert-butyloxycarbonyl)-N$^\omega$-(pyrazinyl-2-carbonyl)-L-lysinyl]thiazolidine-4-carbonitrile (112 mg, 0.25 mmol, 86%).

G. (4R)-3-[N$^\omega$-Pyrazinyl-2-carbonyl)-L-lysinyl]thiazolidine-4-carbonitrile trifluoroacetate (4R)-3-[N$^\alpha$-(tert-Butyloxycarbonyl)-N$^\omega$-(pyrazinyl-2-carbonyl)-L-lysinyl]thiazolidine-4-carbonitrile (110 mg, 0.26 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as (4R)-3-[N$^\omega$-(pyrazinyl-2-carbonyl)-L-lysinyl]thiazolidine-4-carbonitrile trifluoroacetate (57 mg).
[M+H]$^+$=349.1

Example 4

(2S)-1-[N$^\omega$-(Pyridyl-3-methyl)-L-glutaminyl]pyrrolidine-2-carbonitrile dihydrochloride

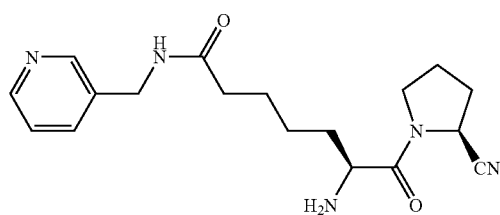

A. (2S)-1-[N-(tert-Butyloxycarbonyl)-O$^\omega$-methyl-L-glutamyl]pyrrolidine-2-carbonitrile N-(tert-Butyloxycarbonyl)-O$^\omega$-methyl-L-glutamic acid (1.0 g, 3.83 mmol) was dissolved in CH$_2$Cl$_2$/DMF (9:1, 20 mL). To this solution at 0° C. were added 1-hydroxybenzotriazole hydrate (788 mg, 5.84 mmol), water-soluble carbodiimide (877 mg, 4.38 mmol), (2S)-pyrrolidine-2-carbonitrile hydrochloride (609 mg, 4.6 mmol) and triethylamine (65 mg, 0.65 mmol). After 18 h at 0° C. to room temperature the solvent was removed in vacuo and the residue was taken up in ethyl acetate (70 mL), this solution was washed with 0.3M KHSO$_4$ (2×20 mL), sat. NaHCO$_3$ (2×20 mL), water (2×20 mL) and brine (1×20 mL (Na$_2$SO$_4$) and evaporated in vacuo. The residue was purified by flash chromatography (eluant: 50% ethyl acetate, 50% pet. ether) to give a brown oil identified as (2S)-1-[N-(tert-butyloxycarbonyl)-O$^\omega$-methyl-L-glutamyl]pyrrolidine-2-carbonitrile (290 mg, 0.86 mmol, 22%).

B. (2S)-1-[N-(tert-Butyloxycarbonyl)-L-glutamyl]pyrrolidine-2-carbonitrile (2S)-1-[N-(tert-Butyloxycarbonyl)-O$^\omega$-methyl-L-glutamyl]pyrrolidine-2-carbonitrile (250 mg, 0.74 mmol) was dissolved in dioxan (5 mL). 1M Lithium hydroxide (1.1 mL, 1.1 mmol) was added. After 1 h at room temperature the solvent was removed in vacuo and the residue was taken up in ethyl acetate (70 mL). This solution was washed with 1M KHSO$_4$ (2×20 mL), water (2×20 mL) and brine (1×20 mL), dried (Na$_2$SO$_4$) and evaporated in vacuo to give a colourless oil identified as (2S)-1-[N-(tert-butyloxycarbonyl)-L-glutamyl]pyrrolidine-2-carbonitrile (200 mg, 0.61 mmol, 83%).

C. (2S)-1-[N$^\alpha$-(tert-Butyloxycarbonyl)-N$^\omega$-(pyridyl-3-methyl)-L-glutaminyl]pyrrolidine-2-carbonitrile (2S)-1-[N-(tert-Butyloxycarbonyl)-L-glutamyl]pyrrolidine-2-carbonitrile (30 mg, 0.093 mmol) was dissolved in CH$_2$Cl$_2$/DMF (9:1, 10 mL). To this solution at 0° C. was added 1-hydroxybenzotriazole hydrate (21 mg, 0.16 mmol), water-soluble carbodiimide (21 mg, 0.105 mmol), 3-(aminomethyl)pyridine (11 mg, 0.1 mmol) and triethylamine(20 mg, 0.2 mmol). After 18 h at 0° C. to room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo to give a yellow oil. The residue was purified by flash chromatography (eluant: 5% methano, 97% chloroform) to give a colourless oil identified as (2S)-1-[N$^\alpha$-(tert-butyloxycarbonyl)-N$^\omega$-(pyridyl-3-methyl)-L-glutaminyl]pyrrolidine-2-carbonitrile (16.6 mg, 0.04 mmol, 44%).

D. (2S)-1-[N$^\omega$-(Pyridyl-3-methyl)-L-glutaminyl]pyrrolidine-2-carbonitrile dihydrochloride (2S)-1-[N$^\alpha$-(tert-Butyloxycarbonyl)-N$^\omega$-(pyridyl-3-methyl)-L-glutaminyl]pyrrolidin-2-carbonitrile (17 mg, 0.04 mmol) was dissolved in 4M HCl/dioxan (5 mL). After 1 h at room temperature the solvent was removed in vacuo to give a white solid identified as (2S)-1-[N$^\omega$-(pyridyl-3-methyl)-L-glutaminyl]pyrrolidine-2-carbonitrile dihydrochloride (17 mg, 0.04 mmol, 100%).
[M+H]$^+$=316.2

Example 5

1-[N$^\omega$-(Pyrazinyl-2-carbonyl)-L-ornithinyl]pyrrolidine trifluoroacetate

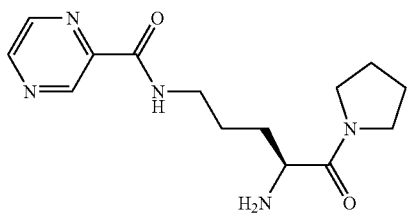

A. 1-[N^ω-(Benzyloxycarbonyl)-N^α-(tert-butyloxycarbonyl)-L-ornithinyl]pyrrolidine N^ω-(Benzyloxycarbonyl)-N^α-(tert-butyloxycarbonyl)-L-ornithine (5.49 g, 15 mmol) was dissolved in CH₂Cl₂/DMF (9:1, 100 mL). To this solution at 0° C. was added 1-hydroxybenzotriazole hydrate (3.37 g, 22 mmol), water-soluble carbodiimide (3.46 g, 18 mmol), pyrrolidine (1.28 g, 18 mmol) and triethylamine (200 mg, 20 mmol). After 18 h at 0° C. to room temperature the solvent was removed in vacuo and the residue was taken up in ethyl acetate (200 mL). The solution was washed with 0.3M KHSO₄ (2×50 mL), sat. NaHCO₃ (2×50 mL), water (2×50 mL) and brine (1×50 mL), dried (Na₂SO₄) and evaporated in vacuo. The residue was purified by flash chromatography (eluant: 90% ethyl acetate, 10% pet. ether) to give a colourless oil identified as 1-[N^ω-(benzyloxycarbonyl)-N^α-(tert-butyloxycarbonyl)-L-ornithinyl]pyrrolidine (5.15 g, 12.3 mmol, 82%).

B. 1-[N^α-(tert-Butyloxycarbonyl)-L-ornithinyl]pyrrolidine

1-[N^ω-(1-(Benzyloxycarbonyl)-N^α-(tert-butyloxycarbonyl)-L-ornithinyl]pyrrolidine (2.15 g, 5.13 mmol) was dissolved in methanol (80 mL). This solution was hydrogenated over 10% Pd/C (400 mg). After 2 h the catalyst was filtered off and washed with methanol (50 mL). The combined filtrates were evaporated in vacuo to give an off white solid identified as 1-[N^α-(tert-butyloxycarbonyl)-L-ornithinyl]pyrrolidine (1.35 g, 4.74 mmol, 94%).

C. 1-[N^α-tert-Butyloxycarbonyl)-N^ω-(pyrazinyl-2-carbonyl)-L-ornithinyl]pyrrolidine 1-[N^α-(tert-Butyloxycarbonyl)-L-ornithinyl]pyrrolidine (100 mg, 0.35 mmol) was dissolved in CH₂Cl₂ (20 mL). To this solution at 0° C. were added PyBroP® (195 mg, 0.4 mmol), 2-pyrazinecarboxylic acid (50 mg, 0.4 mmol) and triethylamine (100 mg, 1.0 mmol). After 18 h at 0° C. to room temperature the solvent was removed in vacuo and the residue was taken up in ethyl acetate (70 mL). The solution was washed with 0.3M KHSO₄ (2×20 mL), sat. NaHCO₃ (2×20 mL), water (2×20 mL) and brine (1×20 mL), dried (Na₂SO₄) and evaporated in vacuo. The residue was purified by flash chromatography (eluant: 3% methanol, 97% chloroform) to give a sticky white solid identified as 1-[N^α-(tert-butyloxycarbonyl)-N^ω-(pyrazinyl-2-carbonyl)-L-ornithinyl]pyrrolidine (90 mg, 0.25 mmol, 66%).

D. 1-[N^ω-(Pyrazinyl-2-carbonyl)-L-ornithinyl]pyrrolidine trifluoroacetate

1-[N^α-(ert-Butyloxycarbonyl)-N^ω-(pyrazinyl-2-carbonyl)-L-ornithinyl]pyrrolidine (90 mg, 0.23 mmol) was dissolved in 4M HCl/dioxan (15 mL). After 45 min at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as 1-[N^ω-(pyrazinyl-2-carbonyl)-L-ornithinyl]pyrrolidine trifluoroacetate (51 mg).

[M+H]⁺=292.1

Example 6

3-[N^ω-(Pyrazinyl-2-carbonyl)-L-ornithinyl]thiazolidine trifluoroacetate

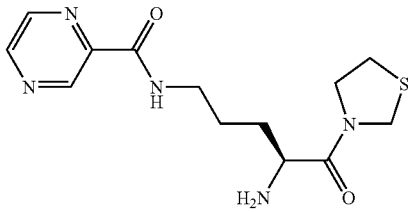

A. 3-[N^α-(tert-Butyloxycarbonyl)-N^ω-(9-fluorenylmethyloxycarbonyl)-L-ornithinyl]thiazolidine N^α-(tert-Butyloxycarbonyl)-N^ω-(9-fluorenylmethyloxycarbonyl)-L-ornithine (2.73 g, 6 mmol) was dissolved in CH₂Cl₂/DMF (9:1, 100 mL). To this solution at 0° C. were added 1-hydroxybenzotriazole hydrate (1.53 g, 10 mmol), water-soluble carbodiimide (1.34 g, 7 mmol), thiazolidine (1.28 g, 18 mmol) and triethylamine (80 mg, 8 mmol). After 18 h at 0° C. to room temperature the solvent was removed in vacuo and the residue was taken up in ethyl acetate (100 mL). The solution was washed with 0.3M KHSO₄ (2×25 mL), sat. NaHCO₃ (2×25 mL), water (2×25 mL) and brine (1×25 mL), dried (Na₂SO₄) and evaporated in vacuo. The residue was purified by flash chromatography (eluant: 75% ethyl acetate, 25% pet. ether) to give a white solid identified as 3-[N^α-(tert-butyloxycarbonyl)-N^ω-(9-fluorenylmethyloxycarbonyl)-L-ornithinyl]thiazolidine (2.55 g, 4.85 mmol, 81%).

B. 3-[N^α-(tert-Butyloxycarbonyl)-L-ornithinyl]thiazolidine

3-[N^α-(tert-Butyloxycarbonyl)-N^ω-(9-fluorenylmethyloxycarbonyl)-L-ornithinyl]thiazolidine (1.15 g, 2.13 mmol) was dissolved in acetonitrile (20 mL). Diethylamine (5 mL) was added. After 90 min at room temperature the solvent was removed in vacuo and the residue was purified by flash chromatography (eluant: 90% chloroform, 7% methanol, 3% triethylamine) to give a pale yellow oil identified as 3-[N^α-(tert-butyloxycarbonyl)-L-ornithinyl]thiazolidine (530 mg, 1.67 mmol, 78%).

C. 3-[N^α-(tert-Butyloxycarbonyl)-N^ω-(pyrazinyl-2-carbonyl)-L-ornithinyl]thiazolidine 3-[N^α-(tert-Butyloxycarbonyl)-L-ornithinyl]thiazolidine (80 mg, 0.27 mmol) was dissolved in CH₂Cl₂ (20 mL). To this solution at 0° C. were added PyBroP® (146 mg, 0.3 mmol), 2-pyrazinecarboxylic acid (37 mg, 0.3 mmol) and triethylamine (90 mg, 0.9 mmol). After 18 h at 0° C. to room temperature the solvent was removed in vacuo and the residue was taken up in ethyl acetate (70 mL). The solution was washed with 0.3M KHSO₄ (2×20 mL), sat. NaHCO₃ (2×20 mL), water (2×20 mL) and brine (1×20 mL), dried (Na₂SO₄) and evaporated in vacuo. The residue was purified by flash chromatography (eluant: 3% methanol, 97% chloroform) to give a sticky white solid identified as 3-[N^α-(tert-butyloxycarbonyl)-N^ω-(pyrazinyl-2-carbonyl)-L-ornithinyl]thiazolidine (45 mg, 0.11 mmol, 41%).

D. 3-[N$^\omega$-(Pyrazinyl-2-carbonyl)-L-ornithinyl]thiazolidine trifluoroacetate 3-[N$^\alpha$-(-(tert-Butyloxycarbonyl)-N$^\omega$-(pyrazinyl-2-carbonyl)-L-ornithinyl]thiazolidine (45 mg, 0.11 mmol) was dissolved in 4M HCl/dioxan (10 mL). After 45 min at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as 3-[N$^\omega$-(pyrazinyl-2-carbonyl)-L-ornithinyl]thiazolidine trifluoroacetate (14 mg).
[M+H]$^+$=310.0

Example 7

(2S)-1-[S-(Acetylaminomethyl)-L-cysteinyl]pyrrolidine-2-carbonitrile trifluoroacetate

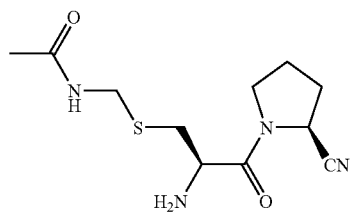

A. (2S)-1-[S-(Acetylaminomethyl)-N-(tert-butyloxycarbonyl)-L-cysteinyl]pyrrolidine-2-carbonitrile S-(Acetylaminomethyl)-N-(tert-butyloxycarbonyl)-L-cysteine (660 mg, 2.26 mmol) was dissolved in CH$_2$Cl$_2$ (30 mL). To this solution at 0° C. were added (2S)-pyrrolidine-2-carbonitrile hydrochloride (250 mg, 1.89 mmol) and PyBOP® (1.3 g, 2.49 mmol), and the pH adjusted to pH9 with triethylamine. After 18 h at 0° C. to room temperature the solvent was removed in vacuo and the residue was taken up in ethyl acetate (150 mL). The solution was washed with 0.3M KHSO$_4$ (2×30 mL), sat. NaHCO$_3$ (2×30 mL), water (2×30 mL) and brine (1×30 mL), dried (Na$_2$SO$_4$) and evaporated in vacuo. The residue was purified by flash chromatography (eluant: 75% ethyl acetate, 25% pet. ether) to give a colourless oil identified as (2S)-1-[S-(acetylaminomethyl)-N-(tert-butyloxycarbonyl)-L-cysteinyl]-pyrrolidine-2-carbonitrile (650 mg, 1.76 mmol, 78%).

B. (2S)-1-[S-(Acetylaminomethyl)-L-cysteinyl]pyrrolidine-2-carbonitrile trifluoroacetate (2S)-1-[S-(Acetylaminomethyl)-N-(tert-butyloxycarbonyl)-L-cysteinyl]pyrrolidine-2-carbonitrile (610 mg, 1.65 mmol) was dissolved in trifluoroacetic acid (30 mL). After 1 h at room temperature the solvent was removed in vacuo to give a colourless oil identified as (2S)-1-[S-(acetylaminomethyl)-L-cysteinyl]pyrrolidine-2-carbonitrile trifluoroacetate (620 mg, 1.61 mmol, 98%).
[M+H]$^+$=271.0

Example 8

(2S)-1-[(2'R)-3'-(Acetylaminomethylthio)-2'-amino-3'-methylbutanoyl]pyrrolidine-2-carbonitrile trifluoroacetate

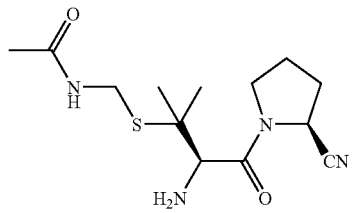

A. (2S)-1-[(2'R)-3'-(Acetylaminomethylthio)-2'-(tert-butyloxycarbonylamino)-3'-methylbutanoyl]pyrrolidine-2-carbonitrile S-(Acetylaminomethyl)-N-(tert-butyloxycarbonyl)penicillamine (720 mg, 2.25 mmol) was dissolved in CH$_2$Cl$_2$ (30 mL). To this solution at 0° C. were added (2S)-pyrrolidine-2-carbonitrile hydrochloride (270 mg, 2.04 mmol) and PyBOP® (1.3 g, 2.49 mmol), and the pH adjusted to pH9 with triethylamine. After 18 h at 0° C. to room temperature the solvent was removed in vacuo and the residue was taken up in ethyl acetate (150 mL). The solution was washed with 0.3M KHSO$_4$ (2×30 mL), sat. NaHCO$_3$ (2×30 mL), water (2×30 mL) and brine (1×30 mL), dried (Na$_2$SO$_4$) and evaporated in vacuo. The residue was purified by flash chromatography (eluant: 75% ethyl acetate, 25% pet. ether) to give a colourless oil identified as (2S)-1-[(2'R)-3'-(acetylaminomethylthio)-2'-(tert-butyloxycarbonylamino)-3'-methylbutanoyl]pyrrolidine-2-carbonitrile (742 mg, 1.86 mmol, 83%).

B. (2S)-1-[(2'-R)-3'-(Acetylaminomethylthio)-2'-amino-3'-methylbutanoyl]pyrrolidine-2-carbonitrile trifluoroacetate (2S)-1-[(2'R)-3'-(Acetylaminomethylthio)-2'-(tert-butyloxycarbonylamino)-3'-methylbutanoyl]pyrrolidine-2-carbonitrile (710 mg, 1.78 mmol) was dissolved in trifluoroacetic acid (30 mL). After 1 h at room temperature the solvent was removed in vacuo to give a colourless oil identified as (2S)-1-[(2'R)-3'-(acetylaminomethylthio)-2'-amino-3'-methylbutanoyl]pyrrolidine-2-carbonitrile trifluoroacetate (560 mg, 1.36 mmol, 76%).
[M+H]$^+$=299.1

Example 9

(2S)-1-[N$^\omega$-(2-Chloropyridyl-3-carbonyl)-L-ornithinyl]pyrrolidine-2-carbonitrile trifluoroacetate

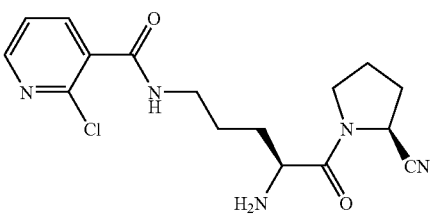

A. (2S)-1-(N$^\alpha$-(tert-Butyloxycarbonyl)-L-ornithyl) pyrrolidine-2-carbonitrile (2S)-1-(N$^\alpha$-(tert-Butyloxycarbonyl)-L-ornithyl)pyrrolidine-2-carbonitrile was prepared by the method described for the lysine derivative in Example 2.

B. (2S)-1-(N$^\alpha$-(tert-Butyloxycarbonyl)-N$^\omega$-(2-chloropyridyl-3-carbonyl)-L-ornithyl)-pyrrolidine-2-carbonitrile (2S)-1-(N$^\alpha$-(tert-Butyloxycarbonyl)-L-ornithyl)pyrrolidine-2-carbonitrile (80 mg, 0.26 mmol) was dissolved in CH$_2$Cl$_2$ (20 mL). To this solution was added 2-chloropyridine-3-carbonyl chloride (55 mg, 0.32 mmol) and the pH adjusted to pH9 with triethylamine. After 18 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 95% ethyl acetate, 5% pet. ether) to give a colourless oil identified as (2S)-1-(N$^\alpha$-(tert-butyloxycarbonyl)-N$^\omega$-(2-chloropyridyl-3-carbonyl)-L-ornithyl)pyrrolidine-2-carbonitrile (60 mg, 0.14 mmol, 53%).

C. (2S)-1-[N$^\omega$-(2-Chloropyridyl-3-carbonyl)-L-ornithinyl]pyrrolidine-2-carbonitrile trifluoroacetate (2S)-1-(N$^\alpha$-(tert-Butyloxycarbonyl)-N$^\omega$-(2-chloropyridyl-3-carbonyl)-L-ornithinyl]pyrrolidine-2-carbonitrile (60 mg, 0.14 mmol) was dissolved in trifluoroacetic acid (5 mL). After 1 h at room temperature the solvent was removed in vacuo. The residue was purified by
[M+H]$^+$=299.1

Example 9

(2S)-1-[N$^\omega$-(2-Chloropyridyl-3-carbonyl)-L-ornithinyl]pyrrolidine-2-carbonitrile trifluoroacetate

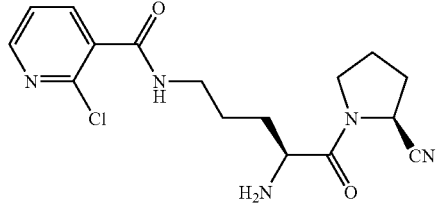

A. (2S)-1-(N$^\alpha$-(tert-Butyloxycarbonyl)-L-ornithyl) pyrrolidine-2-carbonitrile (2S)-1-(N$^\alpha$-(tert-Butyloxycarbonyl)-L-ornithyl)pyrrolidine-2-carbonitrile was prepared by the method described for the lysine derivative in Example 2.

B. (2S)-1-(N$^\alpha$-(tert-Butyloxycarbonyl)-N$^\omega$-(2-chloropyridyl-3-carbonyl)-L-ornithyl)-pyrrolidine-2-carbonitrile (2S)-1-(N$^\alpha$-(tert-Butyloxycarbonyl)-L-ornithyl)pyrrolidine-2-carbonitrile (80 mg, 0.26 mmol) was dissolved in CH$_2$Cl$_2$ (20 mL). To this solution was added 2-chloropyridine-3-carbonyl chloride (55 mg, 0.32 mmol) and the pH adjusted to pH9 with triethylamine. After 18 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 95% ethyl acetate, 5% pet. ether) to give a colourless oil identified as (2S)-1-(N$^\alpha$-(tert-butyloxycarbonyl)-N$^\omega$-(2-chloropyridyl-3-carbonyl)-L-ornithyl)pyrrolidine-2-carbonitrile (60 mg, 0.14 mmol, 53%).

C. (2S)-1-[N$^\omega$-(2-Chloropyridyl-3-carbonyl)-L-ornithinyl]pyrrolidine-2-carbonitrile trifluoroacetate (2S)-1-[N$^\alpha$-(tert-Butyloxycarbonyl)-N$^\omega$-(2-chloropyridyl-3-carbonyl)-L-ornithinyl]pyrrolidine-2-carbonitrile (60 mg, 0.14 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a white solid identified as (2S)-1-[N$^\omega$-(2-chloropyridyl-3-carbonyl)-L-ornithinyl]pyrrolidine-2-carbonitrile trifluoroacetate (52 mg).
[M+H]$^+$=350.1

Example 10

1-[N$^\omega$-(2-Chloropyridyl-3-carbonyl)-L-ornithinyl]pyrrolidine hydrochloride

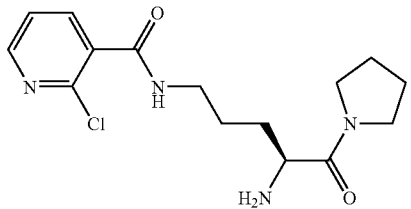

A. 1-(N$^\alpha$-(tert-Butyloxycarbonyl)-N$^\omega$-(2-chloropyridyl-3-carbonyl)-L-ornithyl)pyrrolidine 1-(N$^\alpha$-(tert-Butyloxycarbonyl)-L-ornithyl)pyrrolidine (20 mg, 0.069 mmol) was dissolved in CH$_2$Cl$_2$ (5 mL). To this solution was added 2-chloropyridine-3-carbonyl chloride (14 mg, 0.076 mmol) and the pH adjusted to pH9 with triethylamine. After 1 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 10% methanol, 90% dichloromethane) to give a colourless oil identified as 1-(N$^\alpha$-(tert-butyloxycarbonyl)-N$^\omega$-(2-chloropyridyl-3-carbonyl)-L-ornithyl)pyrrolidine (19 mg, 0.045 mmol, 63%).

B. 1-[N$^\omega$-(2Chloropyridyl-3-carbonyl)-L-ornithinyl]pyrrolidine hydrochloride 1-[N$^\alpha$-(tert-Butyloxycarbonyl)-N$^\omega$-(2-chloropyridyl-3-carbonyl)-L-ornithinyl]pyrrolidine (19 mg, 0.045 mmol) was dissolved in 4M HCl/dioxan (10 mL). After 45 min at room temperature the solvent was removed in vacuo to give a white solid identified as 1-[N$^\omega$-(2-chloropyridyl-3-carbonyl)-L-ornithinyl]pyrrolidine hydrochloride (15 mg).
[M+H]$^+$=325.1

Example 11

3-[N^ω-(2-Chloropyridyl-3-carbonyl)-L-ornithinyl]thiazolidine hydrochloride

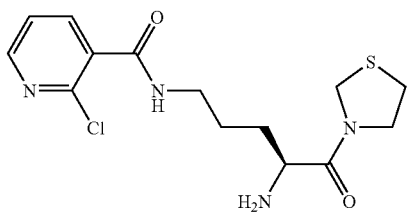

A. 3-(N^α-(tert-Butyloxycarbonyl)-N^ω-(2-chloropyridyl-3-carbonyl)-L-ornithyl)thiazolidine 3-(N^α-(tert-Butyloxycarbonyl)-L-ornithyl)thiazolidine (136 mg, 0.45 mmol) was dissolved in CH$_2$Cl$_2$ (10 mL). To this solution was added 2-chloropyridine-3-carbonyl chloride (88 mg, 0.5 mmol) and the pH adjusted to pH9 with triethylamine. After 1 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 1.5% methanol, 98.5% dichloromethane) to give a colourless oil identified as 3-(N^α-(tert-butyloxycarbonyl)-N^ω-(2-chloropyridyl-3-carbonyl)-L-ornithyl)thiazolidine (30 mg, 0.068 mmol, 15%).

B. 3-[N^ω-(2-Chloropyridyl-3-carbonyl)-L-ornithinyl]thiazolidine hydrochloride 3-[N^α-(tert-Butyloxycarbonyl)-N^ω-(2-chloropyridyl-3-carbonyl)-L-ornithinyl]thiazolidine (30 mg, 0.068 mmol) was dissolved in 4M HCl/dioxan (10 mL). After 45 min at room temperature the solvent was removed in vacuo to give a white solid identified as 1-[N^ω-(2-chloropyridyl-3-carbonyl)-L-ornithinyl]thiazolidine hydrochloride (25 mg).
[M+H]$^+$=342.1

Example 12

(2S)-1-[S-(3-Picolylcarbamoylmethyl)-L-cysteinyl]pyrrolidine-2-carbonitrile trifluoroacetate

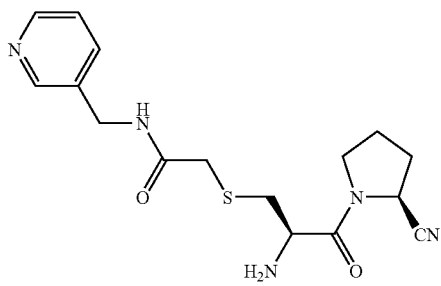

A. S-(Benzyloxycarbonylmethyl)-N-(tert-butyloxycarbonyl)-L-cysteine

N-(tert-Butyloxycarbonyl)-L-cysteine (3.5 g, 15.8 mmol), benzyl 2-bromoacetate (3.7 g, 16.1 mmol) and triethylamine (1.8 g, 18.0 mmol) were dissolved in THF (100 mL). After 18 hours at room temperature the reaction mixture was diluted with ethyl acetate (100 mL), washed with 0.3M KHSO$_4$, sat NaHCO$_3$, water and brine, dried (Na$_2$SO$_4$) and evaporated. The residue was purified by flash chromatography (eluant 95% chloroform, 4% methanol, 1% acetic acid) yielding a colourless oil identified as S-(benzyloxycarbonylmethyl)-N-(tert-butyloxycarbonyl)-L-cysteine (5.2 g, 14.1 mmol, 89%).

B. (2S)-1-[S-(Benzyloxycarbonylmethyl)-N-(tert-butyloxycarbonyl)-L-cysteinyl]pyrrolidine-2-carbonitrile S-(Benzyloxycarbonylmethyl)-N-(tert-butyloxycarbonyl)-L-cysteine (5.10 g, 13.8 mmol) was dissolved in CH$_2$Cl$_2$ (200 mL). This solution was cooled to 0° C., (2S)-pyrrolidine-2-carbonitrile hydrochloride (2.1 g, 15.8 mmol) and PyBOP (8.0 g, 15.3 mmol) were added, and the pH was adjusted to pH9 with triethylamine. After 18 h at 0° C. to room temperature the solvent was removed in vacuo and the residue was taken up in ethyl acetate (150 mL). This solution was washed with 0.3M KHSO$_4$ (1×50 mL), sat. NaHCO$_3$ (1×50 mL), water (1×50 mL) and brine (1×50 mL), dried (Na$_2$SO$_4$) and evaporated in vacuo to give a yellow oil. This was purified by flash chromatography (eluant: 40% ethyl acetate, 60% pet. ether) to give a colourless oil identified as (2S)-1-[S-(benzyloxycarbonylmethyl)-N-(tert-butyloxycarbonyl)-L-cysteinyl]pyrrolidine-2-carbonitrile (5.82 g, 13.0 mmol, 94%).

C. (2S)-1-[N-(tert-Butyloxycarbonyl)-S-(carboxymethyl)-L-cysteinyl]pyrrolidine-2-carbonitrile (2S)-1-[S-(Benzyloxycarbonylmethyl)-N-(tert-butyloxycarbonyl)-L-cysteinyl]pyrrolidine-2-carbonitrile (1.31 g, 2.9 mmol) was dissolved in THF(100 mL). Aqueous lithium hydroxide (1M, 3.5 mL, 3.5 mmol) was added. After 3 hours at room temperature the reaction mixture was diluted with ethyl acetate (100 mL), washed with 1M citric acid, water and brine, dried (Na$_2$SO$_4$) and evaporated in vacuo to give a colourless oil. This was purified by flash chromatography (eluant: 97% chloroform, 2% methanol, 1% acetic acid) to give a colourless oil identified as (2S)-1-[N-(tert-butyloxycarbonyl)-S-(carboxymethyl)-L-cysteinyl]pyrrolidine-2-carbonitrile (860 mg, 2.4 mmol, 82%).

D. (2S)-1[N-(tert-Butyloxycarbonyl)-S-(3-picolylcarbamoylmethyl)-L-cysteinyl]pyrrolidine-2-carbonitrile (2S)-1-[N-(tert-Butyloxycarbonyl)-S-(carboxymethyl)-L-cysteinyl]pyrrolidine-2-carbonitrite (150 mg, 0.42 mmol) was dissolved in CH$_2$Cl$_2$ (20 mL). This solution was cooled to 0° C., 3-(aminomethyl)pyridine (53 mg, 0.5 mmol) and PyBOP (270 mg, 0.52 mmol) were added, and the pH adjusted to pH9 with triethylamine. After 18 h at 0° C. to room temperature the solvent was removed in vacuo and the residue was taken up in ethyl acetate (70 mL). This solution was washed with 0.3M KHSO₄ (1×20 mL), sat. NaHCO₃ (1×20 mL), water (1×20 mL) and brine (1×20 mL), dried (Na₂SO₄) and evaporated in vacuo to give a yellow oil. This was purified by flash chromatography (eluant: 96% chloroform, 4% methanol) to give a colourless oil identified as (2S)-1-[N-(tert-butyloxycarbonyl)-S-(3-picolylcarbamoylmethyl)-L-cysteinyl]pyrrolidine-2-carbonitrile (170 mg, 0.38 mmol, 91%).

E. (2S)-1-[S-(3-Picolylcarbamoylmethyl)-L-cysteinyl]pyrrolidine-2-carbonitrile trifluoroacetate (2S)-1-[N-(tert-Butyloxycarbonyl)-S-(3-picolylcarbamoylmethyl)-L-cysteinyl]pyrrolidine-2-carbonitrile (130 mg, 0.29 mmol) was dissolved in trifluoroacetic acid (10 mL). After 1 hour at room temperature the solvent was removed in vacuo to give a white solid identified as (2S)-1-[S-(3-picolylcarbamoylmethyl)-L-cysteinyl]pyrrolidine-2-carbonitrile trifluoroacetate (116 mg, 0.25 mmol, 86%).

$[M+H]^+=348.2$

Example 13

3-[N$^\omega$-(2-Quinoxaloyl)-L-lysinyl]thiazolidine hydrochloride

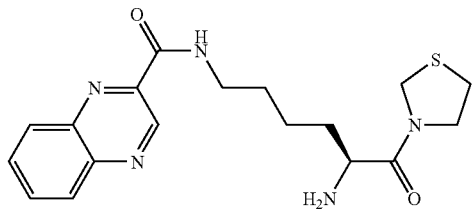

A. 3-[N$^\alpha$-(tert-Butyloxycarbonyl)-N$^\omega$-(2-quinoxaloyl)-L-lysinyl]thiazolidine 3-[N$^\alpha$-(tert-Butyloxycarbonyl)lysinyl]thiazolidine (128 mg, 0.4 mmol) was dissolved in CH₂Cl₂ (10 mL). 2-Quinoxaloyl chloride (85 mg, 0.44 mmol) and potassium carbonate (45.8 mg, 0.3 mmol) were added. The reaction mixture was stirred at room temperature for 18 hours and the solvent removed in vacuo. The residue was purified by flash chromatography (eluant: 99.5% chloroform, 0.5% methanol) to give a colourless oil identified as 3-[N$^\alpha$-(tert-butyloxycarbonyl)-N$^\omega$-(2-quinoxaloyl)-L-lysinyl]thiazolidine (140 mg, 0.296 mmol, 74%).

B. 3-[N$^\omega$-(2-Quinoxaloyl)-L-lysinyl]thiazolidine hydrochloride

3-[N$^\alpha$-(tert-Butyloxycarbonyl)-N$^\omega$-(2-quinoxaloyl)-L-lysinyl]thiazolidine (140 mg, 0.296 mmol) was dissolved in 4M HCl/dioxan (20 mL). After 1 hour at room temperature the solvent was removed in vacuo to give a white solid identified as 3-[N$^\omega$-(2-quinoxaloyl)-L-lysinyl]thiazolidine hydrochloride (128 mg, 0.296 mmol, 100%).

$[M+H]^+=374.2$

Example 14

3-[N$^\omega$-(3-Pyridyloxycarbonyl)-L-ornithinyl]thiazolidine hydrochloride

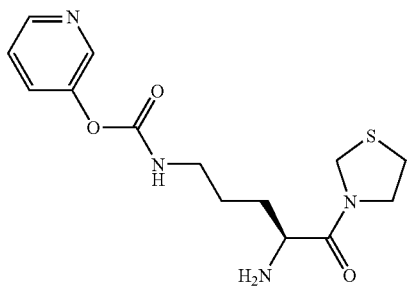

A. 3-[N$^\alpha$-(tert-Butyloxycarbonyl)-N$^\omega$-(3-pyridyloxycarbonyl)-L-ornithinyl]thiazolidine 3-Hydroxypyridine (14.9 mg, 0.138 mmol) was dissolved in CH₂Cl₂ (20 mL). Phosgene (20% solution in toluene, 0.335 mL, 0.685 mmol) and pyridine (14 mg, 0.182 mmol) were added at 0° C. After 90 mins the solvent was removed in vacuo and the residue dissolved in CH₂Cl₂ (20 mL). 3-[N$^\alpha$-(tert-Butyloxycarbonyl)ornithinyl]thiazolidine (42 mg, 0.138 mmol) and triethylamine (28 mg, 0.28 mmol) were added. The reaction mixture was stirred at room temperature for 18 hours and the solvent removed in vacuo. The residue was purified by flash chromatography (eluant: 97% chloroform, 3% methanol) to give a colourless oil identified as 3-[N$^\alpha$-(tert-butyloxycarbonyl)-N$^\omega$-(3-pyridyloxycarbonyl)-L-ornithinyl]thiazolidine (16 mg. 0.038 mmol, 27%).

B. 3-[N$^\omega$-(3-Pyridyloxycarbonyl)-L-ornithinyl]thiazolidine hydrochloride

3-[N$^\alpha$-(tert-Butyloxycarbonyl)-N$^\omega$-(3-pyridyloxycarbonyl)-L-ornithinyl]thiazolidine (16 mg, 0.038 mmol) was dissolved in 4M HCl/dioxan (20 mL). After 1 hour at room temperature the solvent was removed in vacuo to give a white solid identified as 3-[N$^\omega$-(3-pyridyloxycarbonyl)-L-ornithinyl]thiazolidine hydrochloride (14 mg, 0.038 mmol, 100%).

$[M+H]^+=325.1$

Example 15

3-[O-(3-Chlorobenzylcarbamoyl)serinyl]thiazolidine hydrochloride

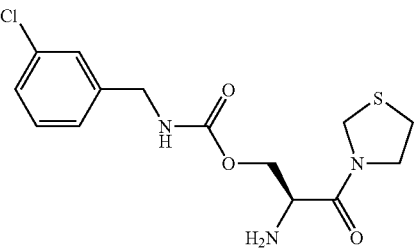

A. 3-[N-(tert-Butyloxycarbonyl)-L-serinyl]thiazolidine

N-(tert-Butyloxycarbonyl)-L-serine (2.1 g, 10.2 mmol) was dissolved in $CH_2Cl_2$/DMF (9:1, 50 mL). Thiazolidine (650 mg, 11.2 mmol), hydroxybenzotriazole(2.8 g, 20.7 mmol) and water soluble carbodiimide (3.9 g, 19.5 mmol) were added at 0° C. The pH was adjusted to pH8 with N-methylmorpholine. The reaction mixture was stirred at room temperature for 18 hours, the solvent removed in vacuo and the residue was taken up in ethyl acetate (150 mL). This solution was washed with 0.3M $KHSO_4$ (1×50 mL), sat. $NaHCO_3$ (1×50 mL), water (1×50 mL) and brine (1×50 mL), dried ($Na_2SO_4$) and evaporated in vacuo to give a white solid identified as 3-[N-(tert-butyloxycarbonyl)-L-serinyl]thiazolidine (2.15 g, 7.78 mmol, 76%).

B. 3-[N-(tert-Butyloxycarbonyl)-O-(3-chlorobenzylcarbamoyl)-L-serinyl]thiazolidine 3-[N-(tert-Butyloxycarbonyl)-L-serinyl]thiazolidine (110 mg, 0.48 mmol) was dissolved in DMF (10 mL) and 1,1'-carbonyl-diimidazole (71 mg, 0.43 mmol) was added. After 2 hours at room temperature 3-chlorobenzylamine (62 mg, 0.4 mmol) was added. After a further 18 hours EtOAc (200 mL) was added. This solution was washed with 0.3M $KHSO_4$ (1×50 mL), sat. $NaHCO_3$ (1×50 mL), water (4×50 mL) and brine (1×50 mL), dried ($Na_2SO_4$) and evaporated in vacuo to give a yellow oil. This was purified by flash chromatography (eluant: 40% ethyl acetate, 60% pet. ether) to give a colourless oil identified as 3-[N-(tert-butyloxycarbonyl)-O-(3-chlorobenzylcarbamoyl)-L-serinyl]thiazolidine (158 mg, 0.36 mmol, 90%).

C. 3-[O-(3-Chlorobenzylcarbamoyl)-L-serinyl]thiazolidine hydrochloride

3-[N-(tert-Butyloxycarbonyl)-O-(3-chlorobenzylcarbamoyl)-L-serinyl]thiazolidine (140 mg, 0.32 mmol) was dissolved in 4M HCl/dioxan (20 mL). After 1 hour at room temperature the solvent was removed in vacuo to give a white solid identified as 3-[O-(3-chlorobenzylcarbamoyl)-L-serinyl]thiazolidine hydrochloride (115 mg, 0.3 mmol, 94%).

$[M+H]^+=344.1$

The Examples set out in the following Tables were prepared by analogous methods to the above.

TABLE 1

Examples 16–162

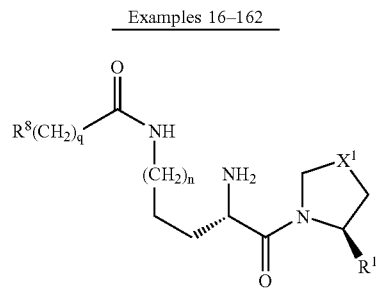

| Example | n | $R^8(CH_2)_q$ | $R^1$ | $X^1$ |
|---|---|---|---|---|
| 16 | 1 | pyridin-3-yl | CN | $CH_2$ |
| 17 | 2 | pyridin-3-yl | CN | $CH_2$ |
| 18 | 1 | pyridin-3-yl | H | S |
| 19 | 2 | pyridin-3-yl | H | S |

TABLE 1-continued

Examples 16–162

| Example | n | $R^8(CH_2)_q$ | $R^1$ | $X^1$ |
|---|---|---|---|---|
| 20 | 1 | pyridin-2-yl | CN | S |
| 21 | 2 | pyridin-2-yl | CN | S |
| 22 | 1 | pyridin-2-yl | H | $CH_2$ |
| 23 | 2 | pyridin-2-yl | H | $CH_2$ |
| 24 | 1 | pyridin-2-yl | CN | $CH_2$ |
| 25 | 2 | pyridin-2-yl | CN | $CH_2$ |
| 26 | 1 | pyridin-2-yl | H | S |
| 27 | 2 | pyridin-2-yl | H | S |
| 28 | 1 | pyridin-4-yl | CN | $CH_2$ |
| 29 | 2 | pyridin-4-yl | CN | $CH_2$ |
| 30 | 1 | pyridin-4-yl | H | S |
| 31 | 2 | pyridin-4-yl | H | S |
| 32 | 1 | 2-chloro-4-trifluoromethylpyrimidin-5-yl | CN | $CH_2$ |
| 33 | 2 | 2-chloro-4-trifluoromethylpyrimidin-5-yl | CN | $CH_2$ |
| 34 | 1 | 2-chloro-4-trifluoromethylpyrimidin-5-yl | H | S |
| 35 | 2 | 2-chloro-4-trifluoromethylpyrimidin-5-yl | H | S |
| 36 | 1 | quinoxalin-2-yl | CN | $CH_2$ |
| 37 | 2 | quinoxalin-2-yl | CN | $CH_2$ |
| 38 | 1 | quinoxalin-2-yl | H | S |
| 39 | 1 | 5-methylpyrazin-2-yl | CN | $CH_2$ |
| 40 | 2 | 5-methylpyrazin-2-yl | CN | $CH_2$ |
| 41 | 1 | 5-methylpyrazin-2-yl | H | S |
| 42 | 2 | 5-methylpyrazin-2-yl | H | S |
| 43 | 1 | 5-bromopyridin-3-yl | CN | $CH_2$ |
| 44 | 2 | 5-bromopyridin-3-yl | CN | $CH_2$ |
| 45 | 1 | 5-bromopyridin-3-yl | H | S |
| 46 | 2 | 5-bromopyridin-3-yl | H | S |
| 47 | 1 | 2-chloropyridin-3-yl | CN | $CH_2$ |
| 48 | 2 | 2-chloropyridin-3-yl | CN | $CH_2$ |
| 49 | 1 | 2-chloropyridin-3-yl | H | S |
| 50 | 2 | 2-chloropyridin-3-yl | H | S |

TABLE 1-continued

Examples 16–162

| Example | n | R⁸(CH₂)q | R¹ | X¹ |
|---|---|---|---|---|
| 51 | 1 | Cl- | CN | CH₂ |
| 52 | 2 | Cl- | CN | CH₂ |
| 53 | 1 | Cl- | H | S |
| 54 | 2 | Cl- | H | S |
| 55 | 1 | (thiophene) | CN | CH₂ |
| 56 | 2 | (thiophene) | CN | CH₂ |
| 57 | 1 | (thiophene) | H | S |
| 58 | 2 | (thiophene) | H | S |
| 59 | 1 | (cyclopentyl) | CN | CH₂ |
| 60 | 2 | (cyclopentyl) | CN | CH₂ |
| 61 | 1 | (cyclopentyl) | H | S |
| 62 | 2 | (cyclopentyl) | H | S |
| 63 | 1 | (benzodioxole) | CN | CH₂ |
| 64 | 2 | (benzodioxole) | CN | CH₂ |
| 65 | 1 | (benzodioxole) | H | S |
| 66 | 2 | (benzodioxole) | H | S |
| 67 | 1 | (isoxazole) | CN | CH₂ |
| 68 | 2 | (isoxazole) | CN | CH₂ |
| 69 | 1 | (isoxazole) | H | S |
| 70 | 2 | (isoxazole) | H | S |
| 71 | 1 | (isoquinoline) | CN | CH₂ |
| 72 | 2 | (isoquinoline) | CN | CH₂ |
| 73 | 1 | (isoquinoline) | H | S |
| 74 | 2 | (isoquinoline) | H | S |
| 75 | 1 | (isoquinoline) | CN | CH₂ |
| 76 | 2 | (isoquinoline) | CN | CH₂ |
| 77 | 1 | (isoquinoline) | H | S |
| 78 | 2 | (isoquinoline) | H | S |
| 79 | 1 | Cl-pyridine | CN | CH₂ |
| 80 | 2 | Cl-pyridine | CN | CH₂ |
| 81 | 1 | Cl-pyridine | H | S |
| 82 | 2 | Cl-pyridine | H | S |
| 83 | 1 | CF₃/Cl-pyridine | CN | CH₂ |
| 84 | 2 | CF₃/Cl-pyridine | CN | CH₂ |
| 85 | 1 | CF₃/Cl-pyridine | H | S |
| 86 | 2 | CF₃/Cl-pyridine | H | S |
| 87 | 1 | NC-pyridine | CN | CH₂ |
| 88 | 2 | NC-pyridine | CN | CH₂ |
| 89 | 1 | NC-pyridine | H | S |
| 90 | 2 | NC-pyridine | H | S |
| 91 | 1 | CF₃-pyridine | CN | CH₂ |
| 92 | 2 | CF₃-pyridine | CN | CH₂ |
| 93 | 1 | CF₃-pyridine | H | S |
| 94 | 2 | CF₃-pyridine | H | S |
| 95 | 1 | (quinoline) | CN | CH₂ |
| 96 | 2 | (quinoline) | CN | CH₂ |
| 97 | 1 | (quinoline) | H | S |
| 98 | 2 | (quinoline) | H | S |
| 99 | 1 | CF₃-pyridine | CN | CH₂ |
| 100 | 2 | CF₃-pyridine | CN | CH₂ |
| 101 | 1 | CF₃-pyridine | H | S |
| 102 | 2 | CF₃-pyridine | H | S |
| 103 | 1 | Cl-pyridine | CN | CH₂ |
| 104 | 2 | Cl-pyridine | CN | CH₂ |
| 105 | 1 | Cl-pyridine | H | S |
| 106 | 2 | Cl-pyridine | H | S |
| 107 | 1 | (quinoline) | CN | CH₂ |
| 108 | 2 | (quinoline) | CN | CH₂ |
| 109 | 1 | (quinoline) | H | S |
| 110 | 2 | (quinoline) | H | S |

TABLE 1-continued

Examples 16–162

| Example | n | R⁸(CH₂)q | R¹ | X¹ |
|---|---|---|---|---|
| 111 | 1 | benzothiophene | CN | CH₂ |
| 112 | 2 | benzothiophene | CN | CH₂ |
| 113 | 1 | benzothiophene | H | S |
| 114 | 2 | benzothiophene | H | S |
| 115 | 1 | hexyl | CN | CH₂ |
| 116 | 2 | hexyl | CN | CH₂ |
| 117 | 1 | hexyl | H | S |
| 118 | 2 | hexyl | H | S |
| 119 | 1 | cyclohexyl | CN | CH₂ |
| 120 | 2 | cyclohexyl | CN | CH₂ |
| 121 | 1 | cyclohexyl | H | S |
| 122 | 2 | cyclohexyl | H | S |
| 123 | 1 | furan | CN | CH₂ |
| 124 | 2 | furan | CN | CH₂ |
| 125 | 1 | furan | H | S |
| 126 | 2 | furan | H | S |
| 127 | 1 | 6-hydroxypyridin-3-yl | H | S |
| 128 | 1 | 3-chloro-6-hydroxypyridin-5-yl | H | S |
| 129 | 2 | 3-chloro-6-hydroxypyridin-5-yl | H | S |
| 130 | 1 | 5,6-dichloropyridin-3-yl | H | S |
| 131 | 2 | 5,6-dichloropyridin-3-yl | H | S |
| 132 | 1 | 5-chloro-6-methylthiopyridin-3-yl | H | S |
| 133 | 1 | 2,6-dichloropyridin-3-yl | H | S |
| 134 | 1 | 2-methyl-6-trifluoromethylpyridin-3-yl | H | S |
| 135 | 1 | 4-(pyridin-4-yl)thiazol-2-yl | H | S |
| 136 | 1 | 3-bromophenyl | H | S |
| 137 | 1 | 3-fluorophenyl | H | S |
| 138 | 1 | 3-cyanophenyl | H | S |
| 139 | 1 | 3-nitrophenyl | H | S |

TABLE 1-continued

Examples 16–162

| Example | n | R⁸(CH₂)q | R¹ | X¹ |
|---|---|---|---|---|
| 140 | 1 | 2,6-dichlorophenyl | H | S |
| 141 | 1 | 4-chlorophenyl | H | S |
| 142 | 1 | 2,3-dimethylphenyl | H | S |
| 143 | 1 | 3,5-bis(trifluoromethyl)phenyl | H | S |
| 144 | 1 | 3-chlorophenyl | H | CH₂ |
| 145 | 1 | 5,6-dichloropyridin-3-yl | H | CH₂ |
| 146 | 1 | 2-chloro-6-methylpyridin-3-yl | H | CH₂ |
| 147 | 1 | 2,6-dichloropyridin-3-yl | H | CH₂ |
| 148 | 1 | 5-chloro-6-methoxypyridin-3-yl | H | S |
| 149 | 1 | 2-carboxypyridin-3-yl | H | S |
| 150 | 2 | 2-carboxypyridin-3-yl | H | S |
| 151 | 1 | 4-chloro-1,3-dimethyl-1H-pyrazolo[3,4-b]pyridin-5-yl | H | S |
| 151 | 2 | 4-chloro-1,3-dimethyl-1H-pyrazolo[3,4-b]pyridin-5-yl | H | S |
| 153 | 1 | 2,6-dimethoxypyridin-3-yl | H | S |
| 154 | 1 | 3-chlorophenyl | H | S |
| 155 | 1 | 3-methylphenyl | H | S |

TABLE 1-continued

Examples 16–162

| Example | n | R⁸(CH₂)q | R¹ | X¹ |
|---|---|---|---|---|
| 156 | 1 | 3-(CF₃)phenyl- | H | S |
| 157 | 1 | 3,5-dichlorophenyl- | H | S |
| 158 | 1 | 1-naphthyl- | H | S |
| 159 | 1 | 4-fluorophenyl- | H | S |
| 160 | 1 | 4-cyanophenyl- | H | S |
| 161 | 1 | 2,3-difluorophenyl- | H | S |
| 162 | 1 | 2,6-dichlorophenyl- | H | CH₂ |

TABLE 2

Examples 163–250

| Example | n | R⁶R⁷N | R¹ | X¹ |
|---|---|---|---|---|
| 163 | 1 | (pyrazin-2-yl)methyl-NH- | CN | CH₂ |
| 164 | 2 | (pyrazin-2-yl)methyl-NH- | CN | CH₂ |
| 165 | 1 | (pyrazin-2-yl)methyl-NH- | H | S |
| 166 | 2 | (pyrazin-2-yl)methyl-NH- | H | S |
| 167 | 1 | (pyrazin-2-yl)methyl-NH- | CN | S |
| 168 | 2 | (pyrazin-2-yl)methyl-NH- | CN | S |
| 169 | 1 | (pyrazin-2-yl)methyl-NH- | H | CH₂ |
| 170 | 2 | (pyrazin-2-yl)methyl-NH- | H | CH₂ |
| 171 | 1 | (pyridin-2-yl)methyl-NH- | CN | CH₂ |
| 172 | 2 | (pyridin-2-yl)methyl-NH- | CN | CH₂ |
| 173 | 1 | (pyridin-2-yl)methyl-NH- | H | S |
| 174 | 2 | (pyridin-2-yl)methyl-NH- | H | S |
| 175 | 1 | (pyridin-3-yl)methyl-NH- | CN | CH₂ |
| 176 | 2 | (pyridin-3-yl)methyl-NH- | CN | CH₂ |
| 177 | 1 | (pyridin-3-yl)methyl-NH- | H | S |
| 178 | 2 | (pyridin-3-yl)methyl-NH- | H | S |
| 179 | 1 | (pyridin-4-yl)methyl-NH- | CN | CH₂ |
| 180 | 2 | (pyridin-4-yl)methyl-NH- | CN | CH₂ |
| 181 | 1 | (pyridin-4-yl)methyl-NH- | H | S |
| 182 | 2 | (pyridin-4-yl)methyl-NH- | H | S |
| 183 | 1 | (pyridin-4-yl)methyl-N(Et)- | CN | CH₂ |
| 184 | 2 | (pyridin-4-yl)methyl-N(Et)- | CN | CH₂ |
| 185 | 1 | (pyridin-4-yl)methyl-N(Et)- | H | S |
| 186 | 2 | (pyridin-4-yl)methyl-N(Et)- | H | S |
| 187 | 1 | 2-(pyridin-2-yl)ethyl-NH- | CN | CH₂ |
| 188 | 2 | 2-(pyridin-2-yl)ethyl-NH- | CN | CH₂ |
| 189 | 1 | 2-(pyridin-2-yl)ethyl-NH- | H | S |
| 190 | 2 | 2-(pyridin-2-yl)ethyl-NH- | H | S |
| 191 | 1 | NH₂ | CN | CH₂ |
| 192 | 2 | NH₂ | CN | CH₂ |
| 193 | 1 | NH₂ | H | S |
| 194 | 2 | NH₂ | H | S |
| 195 | 1 | EtNH- | CN | CH₂ |
| 196 | 2 | EtNH- | CN | CH₂ |
| 197 | 1 | EtNH- | H | S |
| 198 | 2 | EtNH- | H | S |

TABLE 2-continued

Examples 163–250

| Example | n | R⁶R⁷N | R¹ | X¹ |
|---|---|---|---|---|
| 199 | 1 | piperidine | CN | CH₂ |
| 200 | 2 | piperidine | CN | CH₂ |
| 201 | 1 | piperidine | H | S |
| 202 | 2 | piperidine | H | S |
| 203 | 1 | 4-methylpiperazine | CN | CH₂ |
| 204 | 2 | 4-methylpiperazine | CN | CH₂ |
| 205 | 1 | 4-methylpiperazine | H | S |
| 206 | 2 | 4-methylpiperazine | H | S |
| 207 | 1 | benzylamine | CN | CH₂ |
| 208 | 2 | benzylamine | CN | CH₂ |
| 209 | 1 | benzylamine | H | S |
| 210 | 2 | benzylamine | H | S |
| 211 | 1 | N-methylbenzylamine | CN | CH₂ |
| 212 | 2 | N-methylbenzylamine | CN | CH₂ |
| 213 | 1 | N-methylbenzylamine | H | S |
| 214 | 2 | N-methylbenzylamine | H | S |
| 215 | 1 | benzamide | CN | CH₂ |
| 216 | 2 | benzamide | CN | CH₂ |
| 217 | 1 | benzamide | H | S |
| 218 | 2 | benzamide | H | S |
| 219 | 1 | benzenesulfonamide | CN | CH₂ |
| 220 | 2 | benzenesulfonamide | CN | CH₂ |
| 221 | 1 | benzenesulfonamide | H | S |
| 222 | 2 | benzenesulfonamide | H | S |
| 223 | 1 | anilino | CN | CH₂ |
| 224 | 2 | anilino | CN | CH₂ |
| 225 | 1 | anilino | H | S |
| 226 | 2 | anilino | H | S |
| 227 | 1 | pyridin-2-ylamino | CN | CH₂ |
| 228 | 2 | pyridin-2-ylamino | CN | CH₂ |
| 229 | 1 | pyridin-2-ylamino | H | S |
| 230 | 2 | pyridin-2-ylamino | H | S |
| 231 | 1 | 4-methoxyanilino | CN | CH₂ |
| 232 | 2 | 4-methoxyanilino | CN | CH₂ |
| 233 | 1 | 4-methoxyanilino | H | S |
| 234 | 2 | 4-methoxyanilino | H | S |
| 235 | 1 | 3-(dimethylamino)propylamino | CN | CH₂ |
| 236 | 2 | 3-(dimethylamino)propylamino | CN | CH₂ |
| 237 | 1 | 3-(dimethylamino)propylamino | H | S |
| 238 | 2 | 3-(dimethylamino)propylamino | H | S |
| 239 | 1 | N,N-dimethylglycinamide | CN | CH₂ |
| 240 | 2 | N,N-dimethylglycinamide | CN | CH₂ |
| 241 | 1 | N,N-dimethylglycinamide | H | S |
| 242 | 2 | N,N-dimethylglycinamide | H | S |
| 243 | 1 | morpholino | CN | CH₂ |
| 244 | 2 | morpholino | CN | CH₂ |
| 245 | 1 | morpholino | H | S |
| 246 | 2 | morpholino | H | S |
| 247 | 1 | 4-acetylpiperazine | CN | CH₂ |
| 248 | 2 | 4-acetylpiperazine | CN | CH₂ |
| 249 | 1 | 4-acetylpiperazine | H | S |
| 250 | 2 | 4-acetylpiperazine | H | S |

TABLE 3

Examples 251–266

| Example | n | R⁶R⁷N | R¹ | X¹ |
|---|---|---|---|---|
| 251 | 1 | anilino | CN | CH₂ |
| 252 | 2 | anilino | CN | CH₂ |
| 253 | 1 | anilino | H | S |
| 254 | 2 | anilino | H | S |

TABLE 3-continued

Examples 251–266

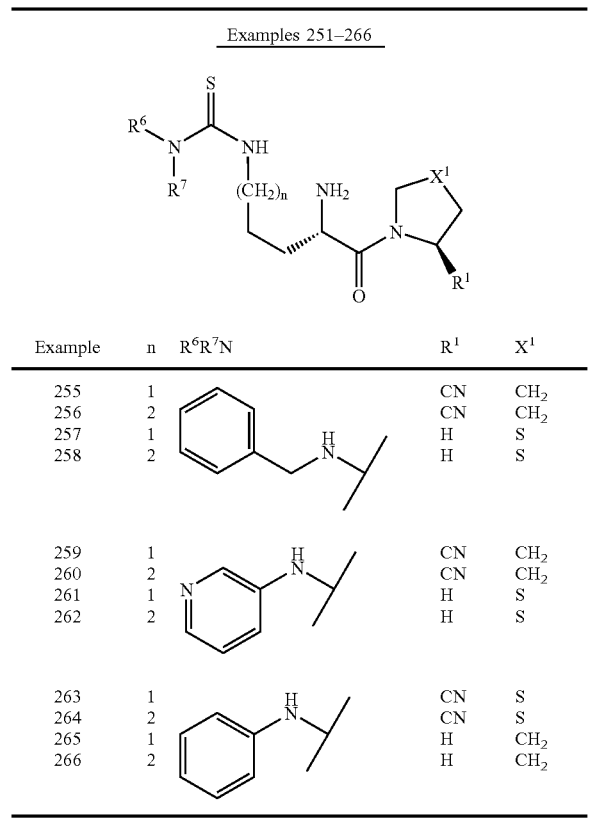

| Example | n | R⁶R⁷N | R¹ | X¹ |
|---|---|---|---|---|
| 255 | 1 | benzyl-NH- | CN | CH₂ |
| 256 | 2 | benzyl-NH- | CN | CH₂ |
| 257 | 1 | benzyl-NH- | H | S |
| 258 | 2 | benzyl-NH- | H | S |
| 259 | 1 | pyridin-3-yl-NH- | CN | CH₂ |
| 260 | 2 | pyridin-3-yl-NH- | CN | CH₂ |
| 261 | 1 | pyridin-3-yl-NH- | H | S |
| 262 | 2 | pyridin-3-yl-NH- | H | S |
| 263 | 1 | phenyl-NH- | CN | S |
| 264 | 2 | phenyl-NH- | CN | S |
| 265 | 1 | phenyl-NH- | H | CH₂ |
| 266 | 2 | phenyl-NH- | H | CH₂ |

TABLE 4

Examples 267–318

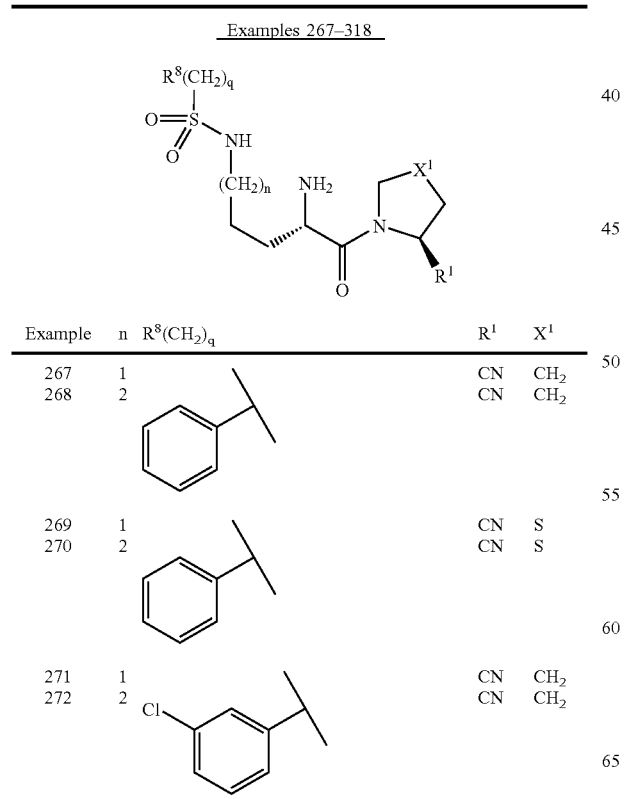

| Example | n | R⁸(CH₂)q | R¹ | X¹ |
|---|---|---|---|---|
| 267 | 1 | phenyl | CN | CH₂ |
| 268 | 2 | phenyl | CN | CH₂ |
| 269 | 1 | phenyl | CN | S |
| 270 | 2 | phenyl | CN | S |
| 271 | 1 | 3-chlorophenyl | CN | CH₂ |
| 272 | 2 | 3-chlorophenyl | CN | CH₂ |

TABLE 4-continued

Examples 267–318

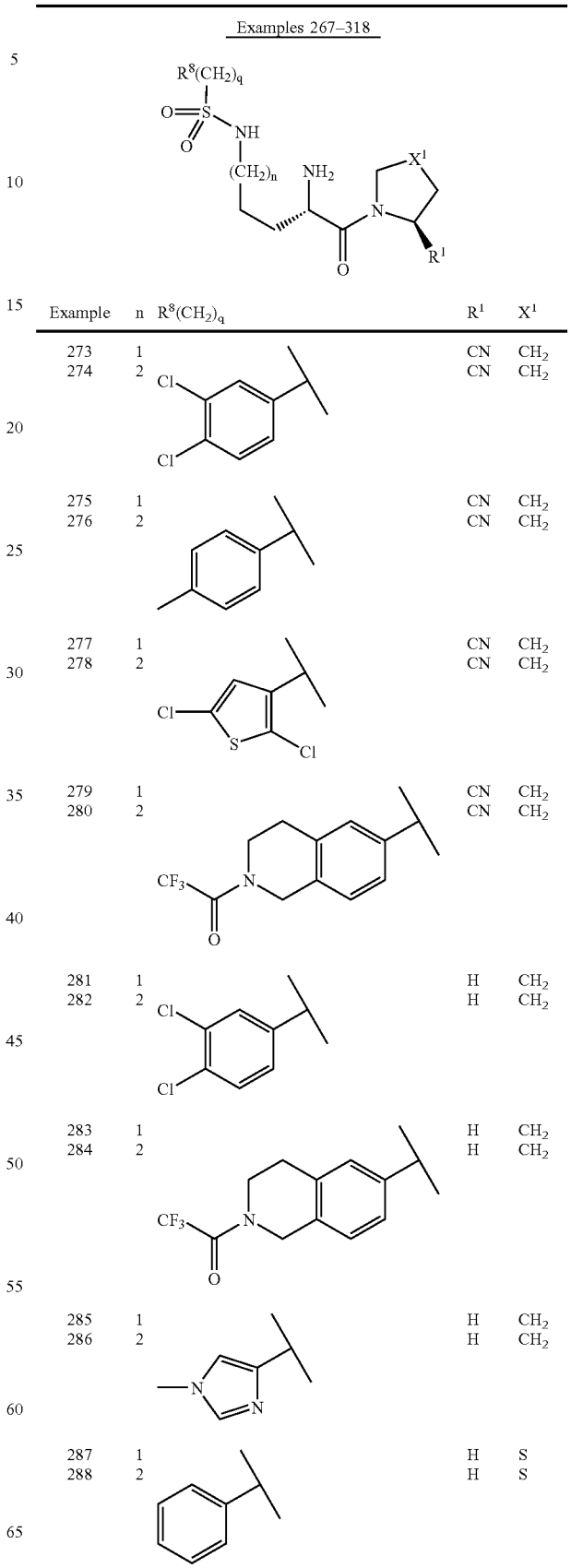

| Example | n | R⁸(CH₂)q | R¹ | X¹ |
|---|---|---|---|---|
| 273 | 1 | 3,4-dichlorophenyl | CN | CH₂ |
| 274 | 2 | 3,4-dichlorophenyl | CN | CH₂ |
| 275 | 1 | 4-methylphenyl | CN | CH₂ |
| 276 | 2 | 4-methylphenyl | CN | CH₂ |
| 277 | 1 | 2,5-dichlorothien-3-yl | CN | CH₂ |
| 278 | 2 | 2,5-dichlorothien-3-yl | CN | CH₂ |
| 279 | 1 | 2-trifluoroacetyl-1,2,3,4-tetrahydroisoquinolin-6-yl | CN | CH₂ |
| 280 | 2 | 2-trifluoroacetyl-1,2,3,4-tetrahydroisoquinolin-6-yl | CN | CH₂ |
| 281 | 1 | 3,4-dichlorophenyl | H | CH₂ |
| 282 | 2 | 3,4-dichlorophenyl | H | CH₂ |
| 283 | 1 | 2-trifluoroacetyl-1,2,3,4-tetrahydroisoquinolin-6-yl | H | CH₂ |
| 284 | 2 | 2-trifluoroacetyl-1,2,3,4-tetrahydroisoquinolin-6-yl | H | CH₂ |
| 285 | 1 | 1-methylimidazol-4-yl | H | CH₂ |
| 286 | 2 | 1-methylimidazol-4-yl | H | CH₂ |
| 287 | 1 | phenyl | H | S |
| 288 | 2 | phenyl | H | S |

TABLE 4-continued

Examples 267–318

| Example | n | R⁸(CH₂)q | R¹ | X¹ |
|---|---|---|---|---|
| 289 | 1 | 3-Cl-C₆H₄-CH₂- | H | S |
| 290 | 2 | 3-Cl-C₆H₄-CH₂- | H | S |
| 291 | 1 | 4-MeO-C₆H₄-CH₂- | H | S |
| 292 | 2 | 4-MeO-C₆H₄-CH₂- | H | S |
| 293 | 1 | C₆H₅-CH₂- | CN | CH₂ |
| 294 | 2 | C₆H₅-CH₂- | CN | CH₂ |
| 295 | 1 | 4-Cl-C₆H₄-CH₂- | CN | CH₂ |
| 296 | 2 | 4-Cl-C₆H₄-CH₂- | CN | CH₂ |
| 297 | 1 | 2-Cl-C₆H₄-CH₂- | CN | CH₂ |
| 298 | 2 | 2-Cl-C₆H₄-CH₂- | CN | CH₂ |
| 299 | 1 | 4-MeO-C₆H₄-CH₂- | CN | CH₂ |
| 300 | 2 | 4-MeO-C₆H₄-CH₂- | CN | CH₂ |
| 301 | 1 | 4-AcNH-C₆H₄-CH₂- | CN | CH₂ |
| 302 | 2 | 4-AcNH-C₆H₄-CH₂- | CN | CH₂ |
| 303 | 1 | 1-methylimidazol-4-yl-CH₂- | CN | CH₂ |
| 304 | 2 | 1-methylimidazol-4-yl-CH₂- | CN | CH₂ |
| 305 | 1 | 3-NC-C₆H₄-CH₂- | CN | CH₂ |
| 306 | 2 | 3-NC-C₆H₄-CH₂- | CN | CH₂ |
| 307 | 1 | 3,4-diCl-C₆H₃-CH₂- | H | S |
| 308 | 2 | 3,4-diCl-C₆H₃-CH₂- | H | S |
| 309 | 1 | 2-(CF₃CO)-1,2,3,4-tetrahydroisoquinolin-6-yl-CH₂- | H | S |
| 310 | 2 | 2-(CF₃CO)-1,2,3,4-tetrahydroisoquinolin-6-yl-CH₂- | H | S |
| 311 | 1 | 1-methylimidazol-4-yl-CH₂- | H | S |
| 312 | 2 | 1-methylimidazol-4-yl-CH₂- | H | S |
| 313 | 1 | 4-Cl-C₆H₄-CH₂- | H | S |
| 314 | 2 | 4-Cl-C₆H₄-CH₂- | H | S |
| 315 | 1 | 2-Cl-C₆H₄-CH₂- | H | S |
| 316 | 2 | 2-Cl-C₆H₄-CH₂- | H | S |
| 317 | 1 | 4-AcNH-C₆H₄-CH₂- | H | S |
| 318 | 2 | 4-AcNH-C₆H₄-CH₂- | H | S |

TABLE 5

Examples 319–378

| Example | R⁴ᴮ | R¹ | X¹ |
|---|---|---|---|
| 319 | NH₂ | CN | CH₂ |
| 320 | diethylamino (N,N-diethyl) | CN | CH₂ |
| 321 | N-benzyl-N-methylamino | CN | CH₂ |
| 322 | (pyrazin-2-yl)methylamino | CN | CH₂ |
| 323 | (pyridin-4-yl)methylamino | CN | CH₂ |
| 324 | 2-(pyridin-2-yl)ethylamino | CN | CH₂ |
| 325 | piperidin-1-yl | CN | CH₂ |
| 326 | morpholin-4-yl | CN | CH₂ |
| 327 | 3-(dimethylamino)propylamino | H | CH₂ |
| 328 | (pyrazin-2-yl)methylamino | H | CH₂ |
| 329 | benzylamino | H | S |
| 330 | (pyridin-3-yl)methylamino | H | S |
| 331 | (pyridin-2-yl)methylamino | H | S |
| 332 | 3-(dimethylamino)propylamino | H | S |
| 333 | butylamino | CN | CH₂ |
| 334 | benzylamino | CN | CH₂ |
| 335 | (pyrazin-2-yl)methylamino | CN | S |
| 336 | (pyrazin-2-yl)methylamino | CN | S |
| 337 | (pyridin-2-yl)methylamino | CN | CH₂ |

TABLE 5-continued

Examples 319–378

| Example | R4B | R1 | X1 |
|---|---|---|---|
| 338 | (thiophen-2-ylmethylamino) | CN | CH2 |
| 339 | (4-methylpiperazin-1-yl)methyl | CN | CH2 |
| 340 | (4-acetylpiperazin-1-yl)methyl | CN | CH2 |
| 341 | N,N-dimethylcarbamoylmethylamino | H | S |
| 342 | (pyrazin-2-ylmethylamino) | H | S |
| 343 | N-benzyl-N-methylamino | H | S |
| 344 | (pyridin-4-ylmethylamino) | H | S |
| 345 | piperidin-1-yl | H | S |
| 346 | N,N-dimethylcarbamoylmethylamino | H | S |
| 347 | (2-chlorobenzylamino) | H | S |
| 348 | (3,4-dichlorobenzylamino) | H | S |
| 349 | (4-chlorobenzylamino) | H | S |
| 350 | (2,5-difluorobenzylamino) | H | S |
| 351 | (4-methoxycarbonylbenzylamino) | H | S |
| 352 | (3-carbamoylbenzylamino) | H | S |
| 353 | (1-phenylethylamino) | H | S |
| 354 | (naphthalen-1-ylmethylamino) | H | S |

TABLE 5-continued

Examples 319–378

| Example | R4B | R1 | X1 |
|---|---|---|---|
| 355 | 2,3-dichlorobenzyl-NH-iPr | H | S |
| 356 | 1,2,3,4-tetrahydroisoquinolin-2-yl-iPr | H | S |
| 357 | 3-chlorobenzyl-NH-iPr | H | S |
| 358 | (S)-1,2,3,4-tetrahydroisoquinoline-3-carboxamide-2-iPr | H | S |
| 359 | 6,7-dimethoxy-1-(cyanomethyl)-1,2,3,4-tetrahydroisoquinolin-2-yl-iPr | H | S |
| 360 | indan-1-yl-NH-iPr | H | S |
| 361 | 1,2,3,4-tetrahydroisoquinoline-3-carboxamide-2-iPr | H | CH2 |
| 362 | 4-chlorobenzyl-NH-iPr | H | CH2 |
| 363 | 3-fluorobenzyl-NH-iPr | H | S |
| 364 | 3-trifluoromethylbenzyl-NH-iPr | H | S |
| 365 | 3,5-bis(trifluoromethyl)benzyl-NH-iPr | H | S |
| 366 | 4-(dimethylamino)benzyl-NH-iPr | H | S |
| 367 | 4-(methylsulfonyl)benzyl-NH-iPr | H | S |
| 368 | 3,5-dichlorobenzyl-NH-iPr | H | S |
| 369 | (S)-1-phenylethyl-NH-iPr | H | S |
| 370 | 4-methylbenzyl-NH-iPr | H | S |

TABLE 5-continued

Examples 319–378

| Example | R⁴ᴮ | R¹ | X¹ |
|---|---|---|---|
| 371 | 3-acetylphenyl-CH₂-NH-iPr | H | S |
| 372 | benzothiophen-2-yl-CH₂-NH-iPr | H | S |
| 373 | 4-chlorobenzyl-NH-iPr | H | S |
| 374 | (1,2,3,4-tetrahydroisoquinolin-3-yl-carboxamide)-iPr | H | S |
| 375 | (1,2,3,4-tetrahydroisoquinolin-3-yl-CH₂OH)-iPr | H | S |
| 376 | (1,2,3,4-tetrahydroisoquinolin-3-yl-carboxamide)-iPr | H | CH₂ |
| 377 | (1,2,3,4-tetrahydroisoquinolin-3-yl-CH₂OH)-iPr | H | CH₂ |
| 378 | 3-chlorobenzyl-NH-iPr | H | CH₂ |

TABLE 6

Examples 379–418

| Example | n | R⁸(CH₂)q | R¹ | X¹ |
|---|---|---|---|---|
| 379 | 1 | pyridin-3-yl-CH₂- | CN | CH₂ |
| 380 | 2 | pyridin-3-yl-CH₂- | CN | CH₂ |
| 381 | 1 | pyridin-4-yl-CH₂- | CN | CH₂ |
| 382 | 2 | pyridin-4-yl-CH₂- | CN | CH₂ |
| 383 | 1 | pyridin-4-yl-CH(CH₃)- | CN | CH₂ |
| 384 | 2 | pyridin-4-yl-CH(CH₃)- | CN | CH₂ |
| 385 | 1 | pyridin-4-yl-(CH₂)₂- | CN | CH₂ |
| 386 | 2 | pyridin-4-yl-(CH₂)₂- | CN | CH₂ |
| 387 | 1 | pyridin-4-yl-(CH₂)₃- | CN | CH₂ |
| 388 | 2 | pyridin-4-yl-(CH₂)₃- | CN | CH₂ |
| 389 | 1 | thiophen-3-yl-CH₂- | CN | CH₂ |
| 390 | 2 | thiophen-3-yl-CH₂- | CN | CH₂ |
| 391 | 1 | N-methylpiperidin-2-yl-CH₂- | CN | CH₂ |
| 392 | 2 | N-methylpiperidin-2-yl-CH₂- | CN | CH₂ |
| 393 | 1 | (CH₃)₂N-CH₂- | CN | CH₂ |
| 394 | 2 | (CH₃)₂N-CH₂- | CN | CH₂ |
| 395 | 1 | pyridin-3-yl-CH₂- | H | CH₂ |
| 396 | 2 | pyridin-3-yl-CH₂- | H | CH₂ |

TABLE 6-continued

Examples 379–418

| Example | n | R⁸(CH₂)q | R¹ | X¹ |
|---|---|---|---|---|
| 397 | 1 | 4-pyridyl-CH₂- | H | S |
| 398 | 2 | 4-pyridyl-CH₂- | H | S |
| 399 | 1 | 3-pyridyl-CH₂- | CN | S |
| 400 | 2 | 3-pyridyl-CH₂- | CN | S |
| 401 | 1 | 2-pyridyl-CH₂- | CN | CH₂ |
| 402 | 2 | 2-pyridyl-CH₂- | CN | CH₂ |
| 403 | 1 | (3-methyl-2-pyridyl)-CH₂- | CN | CH₂ |
| 404 | 2 | (3-methyl-2-pyridyl)-CH₂- | CN | CH₂ |
| 405 | 1 | 2-pyridyl-CH₂CH(CH₃)- | CN | CH₂ |
| 406 | 2 | 2-pyridyl-CH₂CH(CH₃)- | CN | CH₂ |
| 407 | 1 | 2-thienyl-CH₂- | CN | CH₂ |
| 408 | 2 | 2-thienyl-CH₂- | CN | CH₂ |
| 409 | 1 | cyclohexyl-CH₂- | CN | CH₂ |
| 410 | 2 | cyclohexyl-CH₂- | CN | CH₂ |
| 411 | 1 | (1-methylpiperidin-4-yl)-CH₂- | CN | CH₂ |
| 412 | 2 | (1-methylpiperidin-4-yl)-CH₂- | CN | CH₂ |
| 413 | 1 | 3-pyridyl-CH₂- | H | S |
| 414 | 2 | 3-pyridyl-CH₂- | H | S |
| 415 | 1 | 2-pyridyl-CH₂- | H | S |
| 416 | 2 | 2-pyridyl-CH₂- | H | S |

TABLE 6-continued

Examples 379–418

| Example | n | R⁸(CH₂)q | R¹ | X¹ |
|---|---|---|---|---|
| 417 | 1 | 3-thienyl-CH₂- | H | S |
| 418 | 2 | 3-thienyl-CH₂- | H | S |

TABLE 7

Examples 419–438

| Example | m | R⁶R⁷N |
|---|---|---|
| 419 | 1 | 2-(trifluoromethyl)benzyl-NH- |
| 420 | 1 | 3,5-dichlorobenzyl-NH- |
| 421 | 1 | 4-chlorobenzyl-NH- |
| 422 | 1 | 2-chlorobenzyl-NH- |

TABLE 7-continued

Examples 419–438

| Example | m | R⁶R⁷N |
|---|---|---|
| 423 | 1 | 4-(methylsulfonyl)benzyl-N(H)- |
| 424 | 1 | 3-(trifluoromethyl)benzyl-N(H)- |
| 425 | 2 | |
| 426 | 3 | |
| 427 | 1 | 4-methylbenzyl-N(H)- |
| 428 | 2 | |
| 429 | 3 | |
| 430 | 1 | 3,4-dichlorobenzyl-N(H)- |
| 431 | 2 | |
| 432 | 3 | |
| 433 | 2 | 4-fluorobenzyl-N(H)- |
| 434 | 3 | |
| 435 | 2 | 3-fluorobenzyl-N(H)- |
| 436 | 3 | |
| 437 | 2 | 4-methoxybenzyl-N(H)- |
| 438 | 3 | |

TABLE 8

Examples 439–450

| Example | n | R⁸(CH₂)q | R¹ | X¹ |
|---|---|---|---|---|
| 439 | 1 | 3-Cl-phenyl | CN | CH₂ |
| 440 | 2 | 3-Cl-phenyl | CN | CH₂ |
| 441 | 1 | 3,4-diCl-phenyl | CN | CH₂ |
| 442 | 2 | 3,4-diCl-phenyl | CN | CH₂ |
| 443 | 1 | 4-Cl-phenyl | H | S |
| 444 | 2 | 4-Cl-phenyl | H | S |
| 445 | 1 | 2-Cl-phenyl | CN | CH₂ |
| 446 | 2 | 2-Cl-phenyl | CN | CH₂ |
| 447 | 1 | 4-Cl-phenyl | CN | CH₂ |
| 448 | 2 | 4-Cl-phenyl | CN | CH₂ |
| 449 | 1 | 4-MeO-phenyl | CN | CH₂ |
| 450 | 2 | 4-MeO-phenyl | CN | CH₂ |

Example 451

Determination of Activity

Compounds were assayed as inhibitors of DP-IV according to the methods described in WO95/15309. All the compounds described in the foregoing Examples were competitive inhibitors of DP-IV with $K_i$ values less than 300 nM.

Example 452

Determination of Activity in vivo

The anti-diabetic action of selected compounds was demonstrated in Zucker obese rats using a standard oral glucose tolerance test. Control rats were given a solution of glucose by oral gavage, and plasma glucose levels were determined. These rats demonstrated a significant hyperglycaemia. Compounds according to the present invention were dissolved in glucose solution at various concentrations, such that the rats could be given varying doses of the compound simultaneously with the glucose challenge. The hyperglycaemic excursion was reduced in a dose-dependent manner in animals receiving between 0.1 and 100 mg/kg of DP-IV inhibitor.

Example 453

Pharmaceutical Formulation

Tablets containing 100 mg of the compound of Example 1 as the active agent are prepared from the following:

| | |
|---|---|
| Compound of Example 1 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 1.

The above demonstrates that the compounds according to the present invention are inhibitors of DP-IV and would accordingly be expected to be useful as therapeutic agents for the treatment of impaired glucose tolerance, type II diabetes, and other diseases where inhibition of this enzyme leads to an improvement in the underlying pathology or the symptoms.

The present invention is further defined in the following Claims.

The invention claimed is:

1. A pharmaceutical composition comprising a pharmaceutically acceptable excipient and a compound selected from compounds of formula 1, tautomers and stereoisomers thereof, and pharmaceutically acceptable salts of said compounds, tautomers and isomers

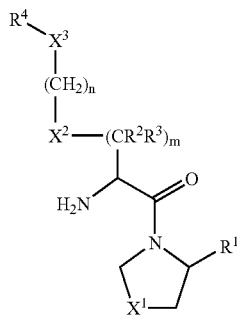

1 wherein:
  $X^1$ is a methylene group;
  $X^2$ is selected from O, S and methylene;
  $X^3$ is either $NR^5$ or a carbonyl or thiocarbonyl group;
  $R^1$ is either a hydrogen atom or a nitrile group;
  $R^2$ and $R^3$ are independently selected from H and $C_1$–$C_6$ alkyl, or together may be —$(CH_2)_p$—;
  $R^4$ is $R^{4A}$ when $X^3$ is $NR^5$ and $R^{4B}$ when $X^3$ is a carbonyl or thiocarbonyl group;
  $R^{4A}$ is selected from $R^6R^7NC(=O)$, $R^6R^7NC(=S)$; $R^8(CH_2)_qC(=O)$, $R^8(CH_2)_qC(=S)$, $R^8(CH_2)_qOC(=O)$ and $R^8(CH_2)_qOC(=S)$;
  $R^{4B}$ is a substituted amino group $R^6R^7N$;
  $R^5$ is H or $C_1$–$C_6$ alkyl;
  $R^6$ and $R^7$ are selected independently from $R^8(CH_2)_q$ or together they are —$(CH_2)_2$-$Z^1$-$(CH_2)_2$— or —$CHR^9$-$Z^2$-$CH_2$—$CHR^{10}$—;
  $R^8$ is selected from H, $C_1$–$C_4$ alkyl, benzo-fused cyclo($C_1$–$C_6$)alkyl, acyl, di($C_1$–$C_6$)alkylcarbamoyl, di($C_1$–$C_6$)alkylamino, N—($C_1$–$C_6$)alkylpiperidyl, optionally substituted aryl, optionally substituted α-($C_1$–$C_6$)alkylbenzyl, optionally substituted aroyl, optionally substituted arylsulphonyl and optionally substituted heteroaryl, wherein heteroaryl means monocyclic five- and six-membered ring aromatic groups with one or two heteroatoms, which are selected from nitrogen, oxygen and sulphur, benzofused derivatives of these rings, and bicyclic groups formed by the fusion of two such monocyclic heteroaromatic groups;
  $R^9$ and $R^{10}$ are selected independently from H, carbamoyl, hydroxymethyl and cyanomethyl;
  $Z^1$ is selected from a covalent bond, —$(CH_2)_r$—, —O—, —$SO_t$— and —$N((CH_2)_qR^8)$—;
  $Z^2$ is an optionally substituted ortho-phenylene moiety;
  m is 1–3;
  n is 0–4;
  p is 2–5;
  q is 0–3;
  r is 1 or 2; and
  t is 0–2;
  the optional substituent(s), if present, are selected from the group consisting of ($C_1$–$C_6$) alkyl, aryl which may be further substituted with one or more methyl or trifluoromethyl groups, hydroxy, ($C_1$–$C_6$)alkyloxy, ($C_1$–$C_6$)alkylsulphonyl, acyl, perfluoroacyl, amino, ($C_1$–$C_6$)alkylamino, di($C_1$–$C_6$)amino, amino($C_1$–$C_6$) alkylene, fluoro, chloro, bromo, trifluoromethyl, nitro, cyano, carbamoyl, carboxy, and ($C_1$–$C_6$)alkyloxycarbonyl groups and/or where two adjacent substituents are present, the two adjacent substituents may be linked so as to form a ring fused to the parent aryl or heteroaryl ring;
  provided that when $X^2$ is $CH_2$, $X^3$ is NH and $R^4$ is $R^8CH_2O(CO)$ then $R^8$ is not unsubstituted phenyl or nitrophenyl; and that when $X^1$ is $CH_2$ and $R^1$ is H and $R^{4A}$ is $R^8(CH_2)_qC(=O)$, then $R^8$ and q are as defined above but are selected so that $R^8(CH_2)_q$ does not represent ($C_1$–$C_4$)alkyl.

2. A pharmaceutical composition according to claim 1 wherein $R^1$ is a nitrile group.

3. A pharmaceutical composition according to claim 2 wherein the stereochemistry of the nitrile group is as shown in formula 2

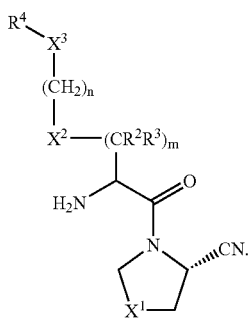

2

4. A pharmaceutical composition according to claim 1 wherein the stereochemistry of the centre adjacent to the primary amine is of the S configuration as shown in formula 3

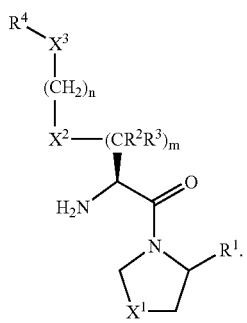

3

5. A pharmaceutical composition according to claim 4 wherein $R^1$ is a nitrile group and the stereochemistry of the nitrile group is as shown in formula 4

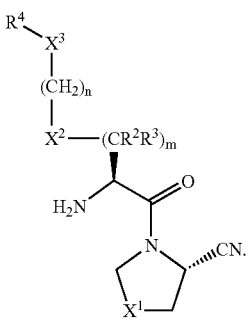

4

6. A pharmaceutical composition according to claim 1 wherein m is 1.

7. A pharmaceutical composition according to claim 1 wherein $R^2$ and $R^3$ are independently H or methyl.

8. A pharmaceutical composition according to claim 1 wherein m is 1, $X^2$ is —$CH_2$— and $R^2$ and $R^3$ are both H.

9. A pharmaceutical composition according to claim 1 wherein m is 1, $X^2$ is —O— and one of $R^2$ and $R^3$ is methyl and the other is H.

10. A pharmaceutical composition according to claim 1 wherein m is 1, $X^2$ is —S— and $R^2$ and $R^3$ are both methyl.

11. A pharmaceutical composition according to claim 1 wherein $X^3$ is NH.

12. A pharmaceutical composition according to claim 11 wherein m is 1, $R^2$ and $R^3$ are H and n is 1 or 2.

13. A pharmaceutical composition according to claim 12 wherein $R^4$ is $R^8CO$ or $R^8NHCO$ and $R^8$ is an optionally substituted heteroaryl, optionally substituted heteroaryl being as defined in claim 1.

14. A pharmaceutical composition according to claim 1 wherein m is 1, $X^2$ is —$CH_2$—, $R^2$ and $R^3$ are both H, n is 0 and $X^3$ is CO.

15. A pharmaceutical composition according to claim 14 wherein $R^4$ is $R^6NH$.

16. A pharmaceutical composition according to claim 15 wherein $R^6$ is an optionally substituted heteroaryl, optionally substituted heteroaryl being as defined in claim 1.

17. A pharmaceutical composition according to claim 13 wherein the heteroaryl group is unsubstituted or mono- or disubstituted and the substituents are selected from $C_1$–$C_6$ alkyl, $C_1$–$C_6$ alkyloxy, fluoro, chloro and trifluoromethyl groups.

18. A pharmaceutical composition according to claim 1 wherein $R^1$ is CN and $X^1$ is $CH_2$.

19. A pharmaceutical composition according to claim 1 wherein $X^3$ is NH and $R^4$ is selected from $R^6R^7N(CO)$, $R^8(CH_2)_qCO$ and $R^8(CH_2)_qSO^2$.

20. A pharmaceutical composition according to claim 1 selected from:
   (2S)-1-[$N^\omega$-(Pyrazinyl-2-carbonyl)-L-ornithinyl]pyrrolidine-2-carbonitrile,
   (2S)-1-[$N^\omega$-(Pyrazinyl-2-carbonyl)-L-lysinyl]pyrrolidine-2-carbonitrile,
   (2S)-[2'S)-2'-Amino-4'-(pyrazinyl-2"-carbonylamino)butanoyl]pyrrolidine-2-carbonitrile,
   (2S)-1-[$N^\omega$-(Pyridyl-3-methyl)-L-glutaminyl]pyrrolidine-2-carbonitrile,
   1-[$N^\omega$-(Pyrazinyl-2-carbonyl)-L-ornithinyl]pyrrolidine,
   (2S)-1-[S-(Acetylaminomethyl)-L-cysteinyl]pyrrolidine-2-carbonitrile,
   1-[$N^\omega$-(2-Chloropyridyl-3-carbonyl)-L-omithinyl]pyrrolidine,
   (2S)-1-[$N^\omega$-(2-Chloropyridyl-3-carbonyl)-L-ornithinyl]pyrrolidine-2-carbonitrile,
   (2S)-1-[(2'R)-3'-(Acetylaminomethylthio)-2'-amino-3'-methylbutanoyl]pyrrolidine-2-carbonitrile, and
   (2S)-1-[S-(3-Picolylcarbamoylmethyl)-L-cysteinyl]pyrrolidine-2-carbonitrile.

21. The pharmaceutical composition of claim 1, wherein the pharmaceutical composition is a liquid.

22. The pharmaceutical composition of claim 21, wherein the pharmaceutical composition is administered orally.

23. The pharmaceutical composition of claim 21, wherein the pharmaceutical composition is administered via an intravenous injection.

24. The pharmaceutical composition of claim 1, wherein the pharmaceutical composition is a solid.

25. The pharmaceutical composition of claim 24, wherein the pharmaceutical composition is covered by an enteric coating.

26. The pharmaceutical composition of claim 24, wherein the pharmaceutically acceptable composition is administered orally.

* * * * *